United States Patent
Matsumoto et al.

(10) Patent No.: US 7,342,105 B2
(45) Date of Patent: Mar. 11, 2008

(54) ANTIBODY AND USE THEREOF

(75) Inventors: Hirokazu Matsumoto, Ibaraki (JP); Eri Hashimoto, Ibaraki (JP); Masaaki Mori, Ibaraki (JP); Chieko Kitada, Osaka (JP)

(73) Assignee: Takeda Chemcial Industries, Ltd., Osaka (JP)

( * ) Notice: Subject to any disclaimer, the term of this patent is extended or adjusted under 35 U.S.C. 154(b) by 0 days.

(21) Appl. No.: 10/547,051

(22) PCT Filed: Feb. 26, 2004

(86) PCT No.: PCT/JP2004/002293

§ 371 (c)(1),
(2), (4) Date: Aug. 25, 2005

(87) PCT Pub. No.: WO2004/076487

PCT Pub. Date: Sep. 10, 2004

(65) Prior Publication Data

US 2006/0177449 A1   Aug. 10, 2006

(30) Foreign Application Priority Data

Feb. 28, 2003   (JP) ............................ 2003-053372

(51) Int. Cl.
*C07K 16/00*   (2006.01)
(52) U.S. Cl. ............... 530/388.1; 530/388.24; 530/391.3; 530/326; 530/328; 435/70.2; 435/70.21; 435/326; 435/331
(58) Field of Classification Search ............ 530/387.1, 530/388.1, 388.24, 391.3, 326, 328; 435/326, 435/70.2, 70.21, 331
See application file for complete search history.

(56) References Cited

U.S. PATENT DOCUMENTS

2004/0110920 A1 * 6/2004 Sato et al.

2005/0048605 A1   3/2005 Mori et al.

FOREIGN PATENT DOCUMENTS

| EP | 1 243 648 A1 | 9/2002 |
| JP | 2001-245666 | 9/2001 |
| JP | 2004-275186 | 10/2004 |
| WO | WO-99/33976 | 7/1999 |
| WO | WO 02/42458 | 5/2002 |

OTHER PUBLICATIONS

Greenspan et al (Nature Biotechnology, 17:936-937, 1999).*
Daniel et al (Virology, 202:540-549, 1994).*
Immunology: A Short Course (Edited by Benjamini et al, p. 40, 1991).*
Boyer et al (Int. J. Cancer, 82:525-531, 1999).*
Molecular Biology of the Cell, (Alberts et al, p. 56, 1983).*
DeGruijl et al. (Nature Medicine, 5(10): 1124-1125, Oct. 1999).*
Bodey et al. (Anticancer Research 20: 2665-2676, 2000).*
Mellman (The Scientist 20(1): 47, 2006).*
Benet et al., pp. 3-32, in Pharmacological Basis of Therapeutics, 8th ed., 1990.*
Jain (Scientific American, 271(1):58-65, Jul. 1994).*
Dillman, (Annals of Internal Medicine, 111:592-603, 1989).*
Weiner (Seminars in Oncology, 26 (4 Suppl 12):41-50, Aug. 1999).*
Fundamental Immunology p. 242 (William E. Paul, M.D. ed., 3d ed; 1993.*

* cited by examiner

*Primary Examiner*—Stephen L. Rawlings
*Assistant Examiner*—Brad Duffy
(74) *Attorney, Agent, or Firm*—Edwards Angell Palmer & Dodge LLP; David G. Conlin; Jonathan M. Sparks

(57) ABSTRACT

The antibody of the present invention, which specifically reacts with the N-terminal or C-terminal partial peptide of TGR23-2 ligand, is useful in detecting and quantifying the TGR23-2 ligand. Moreover, it is useful as a preventing/treating agent and a diagnostic agent for cancer, etc.

8 Claims, 11 Drawing Sheets

ANTIBODY AND USE THEREOF

TECHNICAL FIELD

The present invention relates to a novel antibody, which specifically binds to a polypeptide comprising the amino acid sequence represented by SEQ ID NO: 1, SEQ ID NO: 2 or SEQ ID NO: 3, or a salt of the polypeptide. More particularly, the present invention relates to a method for quantification of the polypeptide based on an antigen-antibody reaction, or a salt of the polypeptide; an antibody useful for diagnosis and development of preventing/treating agents for diseases (e.g., cancer, etc.) associated with the polypeptide or a salt thereof, which utilize a neutralizing activity, and so on.

BACKGROUND ART

Currently, approximately half of the targets of drug development are G protein-coupled receptors (GPCR) characterized by a seven transmembrane domain structure. G protein-coupled receptor TGR23 is a receptor overexpressed in cancer cell lines such as human colon cancer cells LS 174T, LS 180 and SW 403, human gastric cancer cell KATOIII, etc. and colorectal cancer tissues. As ligand peptides for the receptor, there have been found a polypeptide having the amino acid sequence represented by SEQ ID NO: 1 (hereinafter sometimes briefly referred to as human TGR23-2 ligand), a polypeptide having the amino acid sequence represented by SEQ ID NO: 2 (hereinafter sometimes briefly referred to as rat TGR23-2 ligand), a polypeptide having the amino acid sequence represented by SEQ ID NO: 3 (hereinafter sometimes briefly referred to as mouse TGR23-2 ligand), and the like (WO 02/31145).

In order to further clarify the physiological functions of human TGR23-2 ligand, neutralizing antibodies to human TGR23-2 ligand, rat TGR23-2 ligand or mouse TGR23-2 ligand and a simple assay system for detecting/quantifying these TGR23-2 ligands with high sensitivity have been earnestly desired.

DISCLOSURE OF THE INVENTION

As a result of extensive investigations to solve the foregoing problems, the present inventors have found that by producing a plurality of monoclonal antibodies specifically recognizing the N-terminal region and the C-terminal region of human TGR23-2 ligand, rat TGR23-2 ligand or mouse TGR23-2 ligand (preferably, the C-terminal region of rat TGR23-2 ligand or mouse TGR23-2 ligand) and using these antibodies, changes of TGR23-2 ligands in biological components including blood, cerebrospinal fluid, urine, etc. can be detected/quantified in a simple manner with high sensitivity. The inventors have also found that these antibodies can neutralize the activities of TGR23-2 ligands. The present invention has thus come to be accomplished.

That is, the present invention relates to the following features, and so on.

(1) An antibody specifically reacting with a partial peptide at the N-terminal region of a polypeptide or a salt thereof, wherein the polypeptide comprising the amino acid sequence represented by SEQ ID NO: 1, SEQ ID NO: 2 or SEQ ID NO: 3.

(2) The antibody according to (1), which specifically reacts with a peptide having the 1st-7th amino acid sequence in the amino acid sequence represented by SEQ ID NO: 1, SEQ ID NO: 2 or SEQ ID NO: 3.

(3) The antibody according to (1), which specifically reacts with a peptide having the 1st-3rd, 1st-4th, 1st-5th, 1st-6th, 1st-7th, 2nd-4th, 2nd-5th, 2nd-6th, 2nd-7th, 3rd-5th, 3rd-6th, 3rd-7th, 4th-6th, 4th-7th or 5th-7th amino acid sequence in the amino acid sequence represented by SEQ ID NO: 1, SEQ ID NO: 2 or SEQ ID NO: 3.

(3a) The antibody according to (1), which specifically reacts with a peptide having the 1st-8th amino acid sequence in the amino acid sequence represented by SEQ ID NO: 2.

(3b) The antibody according to (1), which specifically reacts with a polypeptide or its amide, or a salt thereof, wherein the polypeptide comprising the amino acid sequence represented by SEQ ID NO: 5.

(4) The antibody according to (1), which does not recognize the partial peptide at the C-terminal region of a polypeptide or a salt thereof, wherein the polypeptide comprising the amino acid sequence represented by SEQ ID NO: 1, SEQ ID NO: 2 or SEQ ID NO: 3.

(5) The antibody according to (1), which has a neutralizing activity for a peptide comprising the amino acid sequence represented by SEQ ID NO: 1, SEQ ID NO: 2 or SEQ ID NO: 3.

(6) The antibody according to (1), which is labeled.

(7) The antibody according to (1), which is a monoclonal antibody.

(8) The monoclonal antibody according to (7), which is represented by 23L-1Na producible from a hybridoma represented by 23L-1N (FERM BP-8302).

(9) An antibody specifically reacting with a partial peptide at the C-terminal region of a polypeptide or a salt thereof, wherein the polypeptide comprising the amino acid sequence represented by SEQ ID NO: 2 or SEQ ID NO: 3.

(10) The antibody according to (9), which specifically reacts with a peptide having the 15th-18th amino acid sequence in the amino acid sequence represented by SEQ ID NO: 2 or SEQ ID NO: 3.

(11) The antibody according to (9), which specifically reacts with a peptide having the 12th-14th, 12th-15th, 12th-16th, 12th-17th, 12th-18th, 13th-15th, 13th-16th, 13th-17th, 13th-18th, 14th-16th, 14th-17th, 14th-18th, 15th-17th, 15th-18th or 16th-18th amino acid sequence in the amino acid sequence represented by SEQ ID NO: 2 or SEQ ID NO: 3.

(12) The antibody according to (9), which does not recognize the partial peptide at the N-terminal region of a polypeptide or a salt thereof, wherein the polypeptide comprising the amino acid sequence represented by SEQ ID NO: 2 or SEQ ID NO: 3.

(13) The antibody according to (9), which has an activity of neutralizing a peptide comprising the amino acid sequence represented by SEQ ID NO: 2 or SEQ ID NO: 3.

(14) The antibody according to (9), which is labeled.

(15) The antibody according to (9), which is a monoclonal antibody.

(16) The monoclonal antibody according to (15), which is represented by 23L-2Ca producible from a hybridoma represented by 23L-2C (FERM BP-8303).

(17) A pharmaceutical comprising the antibody according to (1) or (9).

(18) The pharmaceutical according to (17), which is an agent for preventing/treating cancer or anorexia.

(19) A diagnostic agent comprising the antibody according to (1) and/or (9).

(20) A method of quantifying a polypeptide comprising the amino acid sequence represented by SEQ ID NO: 1, SEQ ID NO: 2 or SEQ ID NO: 3, or a salt thereof, which comprises using the antibody according to (1).

(21) The quantifying method according to (20), wherein the antibody according to (9) is further used.

(22) A method of diagnosis for a disease associated with a polypeptide comprising the amino acid sequence represented by SEQ ID NO: 1, SEQ ID NO: 2 or SEQ ID NO: 3, or a salt thereof, which comprises using the antibody according to (1).

(23) A method of diagnosis for cancer, which comprises using the antibody according to (1).

(24) The method of diagnosis according to (22) or (23), wherein the antibody according to (9) is further used.

(25) A method of quantifying a polypeptide comprising the amino acid sequence represented by SEQ ID NO: 2 or SEQ ID NO: 3, or a salt thereof, which comprises using the antibody according to (9).

(26) A method of quantifying a polypeptide comprising the amino acid sequence represented by SEQ ID NO: 1, SEQ ID NO: 2 or SEQ ID NO: 3, or a salt thereof, in a test fluid, which comprises competitively reacting the antibody according to (1) with a test fluid and a labeled polypeptide comprising the amino acid sequence represented by SEQ ID NO: 1, SEQ ID NO: 2 or SEQ ID NO: 3, or a salt thereof, and determining a ratio of the labeled polypeptide bound to the antibody, or a salt thereof.

(27) A method of quantifying a polypeptide comprising the amino acid sequence represented by SEQ ID NO: 2 or SEQ ID NO: 3, or a salt thereof, in a test fluid, which comprises competitively reacting the antibody according to (9) with a test fluid and a labeled polypeptide comprising the amino acid sequence represented by SEQ ID NO: 2 or SEQ ID NO: 3, or a salt thereof, and determining a ratio of the labeled polypeptide bound to the antibody, or a salt thereof.

(28) A method of quantifying a polypeptide comprising the amino acid sequence represented by SEQ ID NO: 2 or SEQ ID NO: 3, or a salt thereof, in a test fluid, which comprises:
  (i) reacting the antibody according to (1) immobilized on a carrier with a labeled form of the antibody according to (9) and a test fluid and then determining the activity of marker, or
  (ii) reacting the antibody according to (9) immobilized on a carrier with a labeled form of the antibody according to (1) and a test fluid and then determining the activity of marker.

(29) A hybridoma producing the monoclonal antibody according to (7).

(30) The hybridoma according to (29), which is represented by 23L-1N (FERM BP-8302).

(31) A process of producing the monoclonal antibody according to (7), which comprises culturing the hybridoma according to (29) in vivo or in vitro and collecting the monoclonal antibody according to (7) from the body fluid or culture.

(32) A hybridoma, which produces the monoclonal antibody according to (15).

(33) The hybridoma according to (32), which is represented by 23L-2C (FERM BP-8303).

(34) The process of producing the monoclonal antibody according to (15), which comprises culturing the hybridoma according to (32) in vivo or in vitro and collecting the monoclonal antibody according to (15) from the body fluid or culture.

(35) A polypeptide having the amino acid sequence represented by SEQ ID NO: 5, or its amide, or a salt thereof.

(36) A method of preventing/treating cancer or anorexia, which comprises administering an effective dose of the antibody according to (1) or (9) to a mammal.

(37) Use of the antibody according to (1) or (9) to manufacture an agent for preventing/treating cancer or anorexia.

BEST MODE FOR CARRYING OUT THE INVENTION

Figure 1:
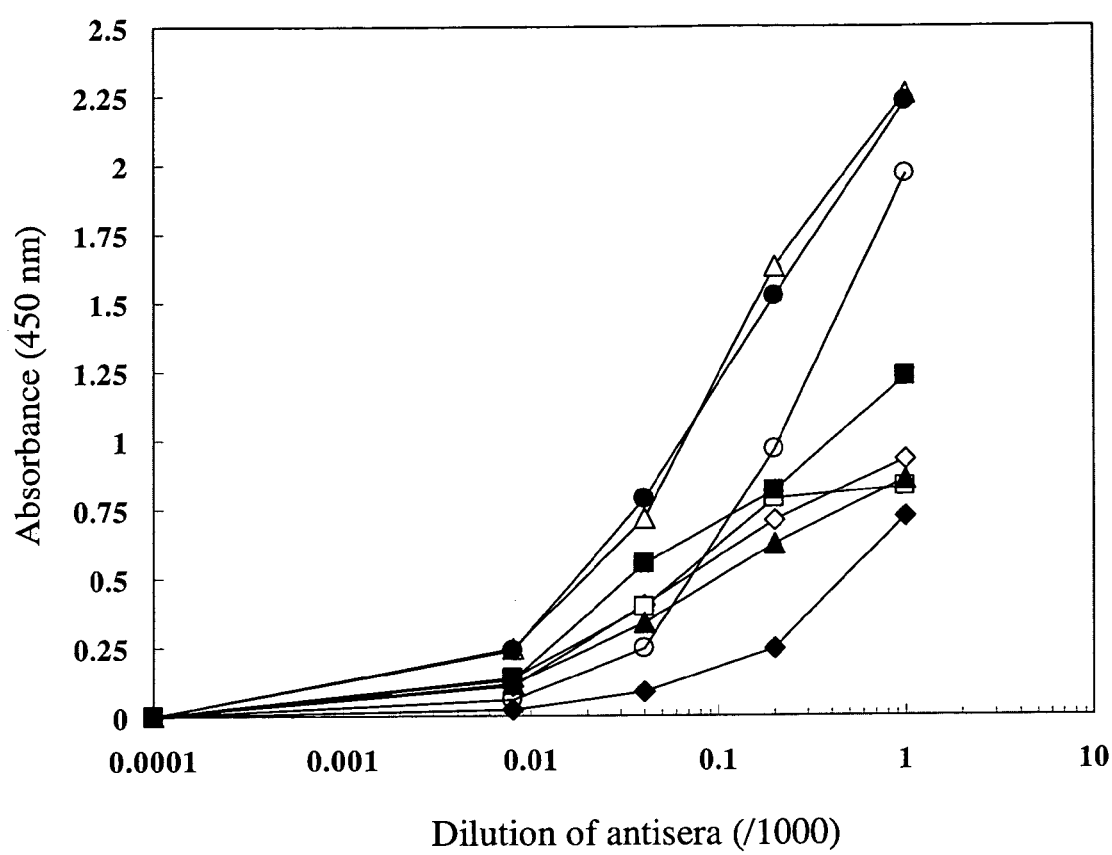
FIG. 1 shows the assay results of antibody titers in antisera of mice immunized with [$Cys^{19}$-$NH_2$] rat TGR23-2 ligand (1-19)-BTG complex. In the figure, -◇-(-open diamond-) represents mouse No. 1, -□-(-open square-) represents mouse No. 2, -△-(-open triangle-) represents mouse No. 3, -○-(-open circle-) represents mouse No. 4, -◆-(-closed diamond-) represents mouse No. 5, -■-(-closed square) represents mouse No. 6, -▲-(-closed triangle-) represents mouse No. 7 and -●-(-closed circle-) represents mouse No. 8.

Throughout the specification, the proteins (polypeptides) are represented in accordance with the conventional way of describing peptides, that is, the N-terminus (amino terminus) at the left hand and the C-terminus (carboxyl terminus) at the right hand. In the proteins used in the present invention including the polypeptide containing the amino acid sequence represented by SEQ ID NO: 1, the C-terminus may be in any form of a carboxyl group, a carboxylate, an amide or an ester.

As the polypeptides comprising the amino acid sequence represented by SEQ ID NO: 1, SEQ ID NO: 2 or SEQ ID NO: 3, there are used polypeptides comprising, for example, (1) the amino acid sequence represented by SEQ ID NO: 1, SEQ ID NO: 2 or SEQ ID NO: 3, wherein several (1 to 5) amino acids are added to the amino acid sequence described above; (2) the amino acid sequence represented by SEQ ID NO: 1, SEQ ID NO: 2 or SEQ ID NO: 3, wherein several (1 to 5) amino acids are inserted into the amino acid sequence described above, (3) the amino acid sequence represented by SEQ ID NO: 1, SEQ ID NO: 2 or SEQ ID NO: 3, wherein several (1 to 5) amino acids in the amino acid sequence described above are replaced with other amino acids, and the like.

As the salts of the polypeptides comprising the amino acid sequences represented by SEQ ID NO: 1, SEQ ID NO: 2 or SEQ ID NO: 3, a salt with physiologically acceptable acid (e.g., inorganic acid, organic acid) or base (e.g., alkali metal, etc.) is used, particularly preferred is physiologically acceptable acid addition salt. Examples of such salts are salts with, for example, inorganic acids (e.g., hydrochloric acid, phosphoric acid, hydrobromic acid or sulfuric acid), salts with organic acids (e.g., acetic acid, formic acid, propionic acid, fumaric acid, maleic acid, succinic acid, tartaric acid, citric acid, malic acid, oxalic acid, benzoic acid, methanesulfonic acid or benzenesulfonic acid), and the like.

Examples of the partial peptides in the N-terminal region of the polypeptide comprising the amino acid sequences represented by SEQ ID NO: 1, SEQ ID NO: 2 or SEQ ID NO: 3, or salts of the polypeptide include:

(a) in the amino acid sequence represented by SEQ ID NO: 1, SEQ ID NO: 2 or SEQ ID NO: 3:
(i) a polypeptide having the 1st-3rd amino acid sequence,
(ii) a polypeptide having the 1st-4th amino acid sequence,
(iii) a polypeptide having the 1st-5th amino acid sequence,
(iv) a polypeptide having the 1st-6th amino acid sequence,
(v) a polypeptide having the 1st-7th amino acid sequence,
(vi) a polypeptide having the 2nd-4th amino acid sequence,
(vii) a polypeptide having the 2nd-5th amino acid sequence,
(viii) a polypeptide having the 2nd-6th amino acid sequence,
(ix) a polypeptide having the 2nd-7th amino acid sequence,
(x) a polypeptide having the 3rd-5th amino acid sequence,
(xi) a polypeptide having the 3rd-6th amino acid sequence,
(xii) a polypeptide having the 3rd-7th amino acid sequence,
(xiii) a polypeptide having the 4th-6th amino acid sequence,
(xiv) a polypeptide having the 4th-7th amino acid sequence and,
(xv) a polypeptide having the 5th-7th amino acid sequence, and, (b) the polypeptide having the 1st-8th amino acid sequence represented by SEQ ID NO: 2, and so on.

Examples of the partial peptides in the C-terminal region of the polypeptide comprising the amino acid sequences represented by SEQ ID NO: 2 or SEQ ID NO: 3, or salts of the polypeptide include, in the amino acid sequence represented by SEQ ID NO: 2 or SEQ ID NO: 3:
(i) a polypeptide having the 12th-14th amino acid sequence,
(ii) a polypeptide having the 12th-15th amino acid sequence,
(iii) a polypeptide having the 12th-16th amino acid sequence,
(iv) a polypeptide having the 12th-17th amino acid sequence,
(v) a polypeptide having the 12th-18th amino acid sequence,
(vi) a polypeptide having the 13th-15th amino acid sequence,
(vii) a polypeptide having the 13th-16th amino acid sequence,
(viii) a polypeptide having the 13th-17th amino acid sequence,
(ix) a polypeptide having the 13th-18th amino acid sequence,
(x) a polypeptide having the 14th-16th amino acid sequence,
(xi) a polypeptide having the 14th-17th amino acid sequence,
(xii) a polypeptide having the 14th-18th amino acid sequence,
(xiii) a polypeptide having the 15th-17th amino acid sequence,
(xiv) a polypeptide having the 15th-18th amino acid sequence and,
(xv) a polypeptide having the 16th-18th amino acid sequence, etc.

The antibodies, which specifically react with partial peptides in the N-terminal region of the polypeptide comprising the amino acid sequence represented by SEQ ID NO: 1, SEQ ID NO: 2 or SEQ ID NO: 3, or salts of the polypeptide, may be those specifically reacting with partial peptides in the N-terminal region of the polypeptide or salts thereof, and preferably are monoclonal antibodies. Specifically, there are used antibodies (preferably, monoclonal antibodies) specifically reacting with peptides comprising the 1st-7th amino acid sequence in the amino acid sequence represented by SEQ ID NO: 1, for example, a polypeptide having the 1st-8th amino acid sequence of the amino acid sequence represented by SEQ ID NO: 2 and the 9th amino acid in this amino acid sequence is substituted with Cys-NH$_2$, or the like. In these antibodies, preferably used are antibodies, which do not recognize partial peptides in the C-terminal region of the polypeptide comprising the amino acid sequence represented by SEQ ID NO: 1, SEQ ID NO: 2 or SEQ ID NO: 3, or salts of the polypeptide.

More preferred are antibodies neutralizing the activity of the polypeptide comprising the amino acid sequence represented by SEQ ID NO: 1, SEQ ID NO: 2 or SEQ ID NO: 3, or salts of the polypeptide.

A specific example of the antibodies which are preferred is the monoclonal antibody represented by 23L-1Na.

As the antibodies, which specifically react with partial peptides in the N-terminal region of the polypeptide comprising the amino acid sequence represented by SEQ ID NO: 1, SEQ ID NO: 2 or SEQ ID NO: 3, or salts of the polypeptide, there are further employed antibodies specifically recognizing (a), in the amino acid sequence represented by SEQ ID NO: 1, SEQ ID NO: 2 or SEQ ID NO: 3, (i) the 1st-3rd amino acid sequence, (ii) the 1st-4th amino acid sequence, (iii) the 1st-5th amino acid sequence, (iv) the 1st-6th amino acid sequence, (v) the 1st-7th amino acid sequence, (vi) the 2nd-4th amino acid sequence, (vii) the 2nd-5th amino acid sequence, (viii) the 2nd-6th amino acid sequence, (ix) the 2nd-7th amino acid sequence, (x) the 3rd-5th amino acid sequence, (xi) the 3rd-6th amino acid sequence, (xii) the 3rd-7th amino acid sequence, (xiii) the 4th-6th amino acid sequence, (xiv) the 4th-7th amino acid sequence and (xv) the 5th-7th amino acid sequence, and (b) the 1st-8th amino acid sequence in the amino acid sequence represented by SEQ ID NO: 2, and the like.

The antibodies that specifically react with partial peptides in the C-terminal region of the polypeptide comprising the amino acid sequence represented by SEQ ID NO: 2 or SEQ ID NO: 3, or salts of the polypeptide may be antibodies, which are specifically reactive with partial peptides in the C-terminal region of the polypeptide comprising the amino acid sequence represented by SEQ ID NO: 2 or SEQ ID NO: 3, or salts of the polypeptide, and preferably monoclonal antibodies. Specifically, there are used antibodies (preferably, monoclonal antibodies) specifically reacting with polypeptides having the amino acid sequence represented by SEQ ID NO: 2 and Cys is added to the 19th amino acid in this amino acid sequence, and the like. In these antibodies, preferably used are antibodies, which do not recognize partial peptides in the N-terminal region of the polypeptide comprising the amino acid sequence represented by SEQ ID NO: 2 or SEQ ID NO: 3, or salts of the polypeptide.

More preferred are antibodies neutralizing the activity of the polypeptide comprising the amino acid sequence represented by SEQ ID NO: 2 or SEQ ID NO: 3, or salts of the polypeptide.

A specific example of the antibodies which are preferred is the monoclonal antibody represented by 23L-2Ca.

Further as the antibodies, which specifically react with partial peptides in the C-terminal region of the polypeptide comprising the amino acid sequence represented by SEQ ID NO: 2 or SEQ ID NO: 3, or salts of the polypeptide, there are employed antibodies specifically recognizing (i) the 12th-14th amino acid sequence, (ii) the 12th-15th amino acid sequence, (iii) the 12th-16th amino acid sequence, (iv) the 12th-17th amino acid sequence, (v) the 12th-18th amino acid sequence, (vi) the 13th-15th amino acid sequence, (vii) the 13th-16th amino acid sequence, (viii) the 13th-17th amino acid sequence, (ix) the 13th-18th amino acid sequence, (x) the 14th-16th amino acid sequence, (xi) the 14th-17th amino acid sequence, (xii) the 14th-18th amino acid sequence, (xiii) the 15th-17th amino acid sequence and (xiv) the 15th-18th amino acid sequence, and (xv) the 16th-18th amino acid sequence, in the amino acid sequence represented by SEQ ID NO: 2 or SEQ ID NO: 3; and the like.

Hereinafter, preparation of antigens for antibodies specifically reacting with partial peptides in the N-terminal region of the polypeptide or a salt thereof, wherein the polypeptide comprising the amino acid sequence represented by SEQ ID NO: 1, SEQ ID NO: 2 or SEQ ID NO: 3, and antibodies specifically reacting with partial peptides in the C-terminal region of the polypeptide or a salt thereof, wherein the polypeptide comprising the amino acid sequence represented by SEQ ID NO: 2 or SEQ ID NO: 3 (hereinafter these antibodies are sometimes simply referred to as the antibody of the present invention) and preparation of these antibodies are explained below.

(1) Preparation of Antigen

To prepare the antibody of the present invention, any antigen such as synthetic peptides having 1 or 2 more antigenic determinants, which are the same as in the polypeptide or a salt thereof, wherein the polypeptide comprising the amino acid sequence represented by SEQ ID NO: 1, SEQ ID NO: 2 or SEQ ID NO: 3 (hereinafter sometimes merely referred to as TGR23-2 ligand), etc. may be used (hereinafter these antigens are sometimes referred to as the TGR23-2 ligand antigen).

The TGR23-2 ligand can be (a) prepared from mammalian tissue or cells of human, monkey, rat, mouse, etc., by publicly known methods or with some modifications, (b) chemically synthesized by publicly known peptide synthesis methods using a peptide synthesizer, etc., or (c) produced by culturing a transformant bearing a DNA encoding the TGR23-2 ligand.

(a) Where the TGR23-2 ligand antigen is prepared from the mammalian tissues or cells, the tissues or cells are homogenized, then extracted with an acid, an alcohol, etc., and the extract is purified and isolated by a combination of salting-out, dialysis, gel filtration, chromatography techniques such as reverse phase chromatography, ion exchange chromatography, affinity chromatography and the like.

(b) Where the TGR23-2 ligand antigen is prepared chemically, the synthetic peptides used are, for example, a peptide having the same structure as the TGR23-2 ligand antigen purified from natural one as described above, a peptide containing 1 or 2 more amino acid sequences, which are the same amino acid sequences consisting of at least 3, preferably at least 8 amino acids in an optional region of the amino acid sequence represented by SEQ ID NO: 1, etc.

(c) Where the TGR23-2 ligand are prepared using the DNA-bearing transformants, the DNA can be produced in accordance with publicly known cloning techniques [e.g., the method described in Molecular Cloning (2nd ed., J.

Sambrook et al., Cold Spring Harbor Lab. Press, 1989), etc.]. The cloning techniques include (1) a method in which transformants containing DNAs encoding the TGR23-2 ligand are obtained from cDNA library by hybridization using DNA probes or DNA primers designed based on the amino acid sequence of TGR23-2 ligand, or (2) a method in which transformants containing DNAs encoding the TGR23-2 ligand are obtained by PCR using DNA primers designed based on the amino acid sequence of TGR23-2 ligand, etc.

Peptides used as the TGR23-2 ligand antigen can be prepared (1) by peptide synthesis methods publicly known, or (2) by cleaving peptides having the amino acid sequence represented by SEQ ID NO: 1, SEQ ID NO: 2 or SEQ ID NO: 3 with an appropriate peptidase.

For the methods for peptide synthesis, for example, any of solid phase synthesis and liquid phase syntheses may be used. That is, the partial peptides or amino acids that can construct the peptide are condensed with the remaining part, and where the product contains protecting groups, the protecting groups are removed, to give the desired peptide. By the condensation or removal of the protecting groups, objective peptides can be prepared. Publicly known methods for condensation and removal of the protecting groups are methods described in (i) or (ii) below.

(i) Peptide Synthesis, Interscience Publishers, New York (1966)

(ii) The Peptide, Academic Press, New York (1965)

After the reaction, the peptide may be purified and isolated by a combination of conventional purification methods such as solvent extraction, distillation, column chromatography, liquid chromatography, recrystallization, etc. to give the peptide. When the peptide obtained by the above methods is in a free form, the peptide can be converted into an appropriate salt by a publicly known method; when the peptide is obtained in a salt form, it can be converted into a free form by a publicly known method.

Amides of the peptide may be obtained using commercially available resins for peptide synthesis, which are suitable for formation of the amides. Examples of such resins include chloromethyl resin, hydroxymethyl resin, benzhydrylamine resin, aminomethyl resin, 4-benzyloxybenzyl alcohol resin, 4-methylbenzhydrylamine resin, PAM resin, 4-hydroxymethylmehtylphenyl acetamidomethyl resin, polyacrylamide resin, 4-(2',4'-dimethoxyphenylhydroxymethyl)phenoxy resin, 4-(2',4'-dimethoxyphenyl-Fmoc-aminoethyl)phenoxy resin, etc. Using these resins, amino acids in which α-amino groups and functional groups on the side chains are appropriately protected are condensed on the resin in the order of the sequence of the objective peptide according to various condensation methods publicly known in the art. At the end of the reaction, the peptide is cut out from the resin and at the same time, the protecting groups are removed to obtain the objective peptide. Alternatively, the objective peptide may also be obtained by taking out the peptide protected in part with chlorotrityl resin, oxime resin, 4-hydroxybenzoic acid type resin, etc., and deprotecting the protective groups in a conventional manner.

For condensation of the protected amino acids described above, a variety of activation reagents available for the polypeptide synthesis may be used, and carbodiimides are particularly preferably employed. Examples of such carbodiimides include DCC, N,N'-diisopropylcarbodiimide, N-ethyl-N'-(3-dimethylaminopropyl)-carbodiimide, etc. For activation by these reagents, the protected amino acids in combination with a racemization inhibitor (e.g., HOBt, HOOBt, etc.) are added directly to the resin, or the protected amino acids are previously activated in the form of symmetric acid anhydrides, HOBt esters or HOOBt esters, followed by adding the thus activated protected amino acids to the resin. Solvents used to activate the protected amino acids or condense with the resin may be chosen from solvents that are known to be usable for polypeptide condensation reactions. For example, there may be employed acid amides such as N,N-dimethylformamide, N,N-dimethylacetamide, N-methylpyrrolidone, etc.; halogenated hydrocarbons such as methylene chloride, chloroform, etc.; alcohols such as trifluoroethanol, etc.; sulfoxides such as dimethylsulfoxide, etc.; tertiary amines such as pyridine etc.; ethers such as dioxan, tetrahydrofuran, etc.; nitriles such as acetonitrile, propionitrile, etc.; esters such as methyl acetate, ethyl acetate, etc.; and appropriate mixtures of these solvents. The reaction temperature is appropriately chosen from the range known to be applicable to peptide bond-forming reactions and is usually selected in the range of approximately −20° C. to 50° C. The activated amino acid derivatives are used generally in an excess of 1.5 to 4 times. The condensation is examined using the ninhydrin reaction; when the condensation is insufficient, the condensation can be completed by repeating the condensation reaction without removal of the protecting groups. When the condensation is yet insufficient even after repeating the reaction, the unreacted amino acids may be acetylated using acetic anhydride or acetylimidazole thereby to cancel any adverse effects on subsequent reactions.

Examples of the protecting groups used to protect the amino groups of the starting amino acids include Z, Boc, t-pentyloxycarbonyl, isobornyloxycarbonyl, 4-methoxybenzyloxycarbonyl, Cl-Z, Br-Z, adamantyloxycarbonyl, trifluoroacetyl, phthaloyl, formyl, 2-nitrophenylsulphenyl, diphenylphosphinothioyl, Fmoc, etc. Examples of the protecting groups of a carboxyl group include, in addition to a $C_{1-6}$ alkyl group, a $C_{3-8}$ cycloalkyl group, a $C_{7-14}$ aralkyl group, 2-adamantyl, 4-nitrobenzyl, 4-methoxybenzyl, 4-chlorobenzyl, phenacyl and benzyloxycarbonyl hydrazide, t-butoxycarbonyl hydrazide, trityl hydrazide, and the like.

The hydroxyl group of serine and threonine can be protected through, for example, its esterification or etherification. Examples of the groups suitable for the esterification include a lower ($C_{1-6}$) alkanoyl group, such as acetyl group, etc.; an aroyl group such as benzoyl group, etc., and a group derived from carbonic acid such as benzyloxycarbonyl group, ethoxycarbonyl group, etc. Examples of a group suitable for the etherification include benzyl group, tetrahydropyranyl group, t-butyl group, etc.

Examples of groups for protecting the phenolic hydroxyl group of tyrosine include Bzl, Cl-Bzl, -2-nitrobenzyl, Br-Z, t-butyl, etc.

Examples of groups used to protect the imidazole moiety of histidine include Tos, 4-methoxy-2,3,6-trimethylbenzenesulfonyl, DNP, Bom, Bum, Boc, Trt, Fmoc, etc.

Examples of the activated carboxyl groups in the starting compounds include the corresponding acid anhydrides, azides, activated esters [esters with alcohols (e.g., pentachlorophenol, 2,4,5-trichlorophenol, 2,4-dinitrophenol, cyanomethyl alcohol, p-nitrophenol, HONB, N-hydroxysuccimide, N-hydroxyphthalimide, HOBt)]. As the activated amino acids, in which the amino groups are activated in the starting material, the corresponding phosphoric amides are employed.

To eliminate (split off) the protecting groups, there are used catalytic reduction under hydrogen gas flow in the presence of a catalyst such as Pd-black, Pd-carbon, etc.; an acid treatment with anhydrous hydrofluoric acid, methanesulfonic acid, trifluoromethane-sulfonic acid or trifluoroacetic acid, or a mixture solution of these acids; a treatment with a base such as diisopropylethylamine, triethylamine, piperidine, piperazine, etc.; and reduction with sodium in liquid ammonia; or the like. The elimination of the protecting groups by the acid treatment described above is carried out generally at a temperature of approximately −20° C. to 40° C. In the acid treatment, it is efficient to add a cation scavenger such as anisole, phenol, thioanisole, m-cresol, p-cresol, dimethylsulfide, 1,4-butanedithiol, 1,2-ethanedithiol, etc.

Furthermore, 2,4-dinitrophenyl group known as the protecting group for the imidazole of histidine is removed by a treatment with thiophenol. Formyl group used as the protecting group of the indole of tryptophan is eliminated by the aforesaid acid treatment in the presence of 1,2-ethanedithiol, 1,4-butanedithiol, etc. as well as by a treatment with an alkali such as a dilute sodium hydroxide solution, dilute ammonia, etc.

Protection of the functional groups that should not be involved in the reaction of the starting materials, protecting groups, elimination of the protecting groups and activation of the functional groups involved in the reaction may be appropriately chosen from publicly known groups and publicly known means.

In another method for obtaining the amides of the peptide, for example, the α-carboxyl group of the carboxy terminal amino acid is first protected by amidation; the peptide chain is then extended to a desired length toward the amino group side. Thereafter, a peptide in which only the protecting group of the N-terminal α-amino group in the peptide chain has been eliminated from the peptide and a peptide (or amino acids) in which only the protecting group of the C-terminal carboxyl group has been eliminated are prepared. The two peptides are condensed in a mixture of the solvents described above. The details of the condensation reaction are the same as described above. After the protected peptide obtained by the condensation is purified, all the protecting groups are eliminated by the method described above to give the desired crude peptide. This crude peptide is purified by various known purification means. Lyophilization of the major fraction gives the amide of the desired peptide.

To prepare the esterified peptide, for example, the α-carboxyl group of the carboxy terminal amino acid is condensed with a desired alcohol to prepare the amino acid ester, which is followed by procedure similar to the preparation of the amidated peptide above to give the ester form of the desired peptide.

The TGR23-2 ligand antigen may be provided for direct immunization in its immobilized form. The TGR23-2 ligand antigen may also be bound or adsorbed to an appropriate carrier and the complex produced can be provided for immunization. A mixing ratio of the carrier to the TGR23-2 ligand antigen (hapten) may be in any ratio of any type, as long as the antibody can be efficiently produced to the TGR23-2 ligand antigen bound or adsorbed to the carrier. A high molecular carrier, which is conventionally used to produce an antibody to a hapten antigen, bound or adsorbed to the hapten in a weight ratio of 0.1 to 100 based on 1 of hapten may be used. As such a high molecular carrier, there are used a naturally occurring high molecular carrier and a synthetic high molecular carrier. Examples of the naturally occurring high molecular carrier used are serum albumin from mammals such as bovine, rabbit, human, etc., thyroglobulins from mammals such as bovine, rabbit, etc., hemoglobins from mammals such as bovine, rabbit, human, sheep, etc., or keyhole limpet hemocyanin. Examples of the synthetic high molecular carrier, which can be used, are various latexes including polymers, copolymers, etc., for example, polyamino acids, polystyrenes, polyacryls, polyvinyls, polypropylenes, etc.

For coupling of the hapten and the carrier, a variety of condensing agents can be used. Examples of the condensing agents, which are advantageously employed, are diazonium compounds such as bis-diazotized benzidine capable of crosslinking tyrosines, histidines or tryptophans; dialdehyde compounds such as glutaraldehyde, etc. capable of crosslinking amino groups with each other; diisocyanate compounds such as toluene-2,4-diisocyanate, etc.; dimaleimide compounds such as N,N'-o-phenylenedimaleimide, etc. capable of crosslinking thiols with each other; maleimide activated ester compounds capable of crosslinking an amino group with a thiol group; carbodiimide compounds capable of crosslinking an amino group with a carboxyl group; etc. In the crosslinking of amino groups with each other, one amino group is reacted with an activated ester reagent (e.g., SPDP, etc.) having dithiopyridyl group and then reduced to introduce the thiol group, whereas another amino group is introduced with a maleimide group using a maleimide activated ester reagent, and the two groups may be reacted with each other.

(2) Preparation of Monoclonal Antibody

The TGR23-2 ligand antigen is administered to warm-blooded animal either solely or together with carriers or diluents to the site where the production of antibody is possible by administration routes such as intraperitoneally, intravenously, subcutaneously, etc. In order to potentiate the antibody productivity upon the administration, complete Freund's adjuvants or incomplete Freund's adjuvants may be administered. The administration is usually carried out once in every 2 to 6 weeks and approximately 2 to 10 times in total. Examples of the warm-blooded animal are simian, rabbits, canine, guinea pigs, mice, rats, sheep, goats, fowl, etc. with mice being preferred for the preparation of monoclonal antibodies.

In the preparation of monoclonal antibodies, from warm-blooded animals, e.g., mice, immunized with the TGR23-2 ligand antigen, the animal wherein the antibody titer is noted is selected, then the spleen or lymph node is collected after 2 to 5 days from the final immunization and antibody-producing cells contained therein are fused with myeloma cells to give anti-TGR23-2 ligand monoclonal antibody-producing hybridomas. Measurement of the anti-TGR23-2 ligand antibody titer in sera is made, for example, by reacting a labeled form of the TGR23-2 ligand, which will be described later, with the antiserum followed by assaying the activity of a marker bound to the antibody. The fusion may be operated, for example, by the known Kohler and Milstein method [Nature, 256, 495 (1975)]. Examples of fusion accelerators are polyethylene glycol (PEG), Sendai virus, etc., of which PEG is preferably employed. Examples of the myeloma cells are NS-1, P3U1, SP2/0, AP-1, etc. In particular, P3U1 or the like is preferably employed. A preferred ratio in count of the antibody-producing cells (spleen cells) to the myeloma cells used is within a range of approximately 1:1 to 20:1. When PEG (preferably, PEG 1000 to PEG 6000) is added in a concentration of approximately 10 to 80% followed by incubation generally at 20 to 40° C., preferably at 30 to 37° C. generally for 1 to 10 minutes, an efficient cell fusion can be carried out.

Various methods can be used for screening of the anti-TGR23-2 ligand antibody-producing hybridomas. Examples of such methods include a method which comprises adding the hybridoma culture supernatant to a solid phase (e.g., microplate) adsorbed with the TGR23-2 ligand or partial peptides thereof directly or together with a carrier, then adding an anti-immunoglobulin antibody (when mouse cells are used for the cell fusion, anti-mouse immunoglobulin antibody is used) labeled with a radioactive substance, an enzyme or the like, or Protein A and detecting the anti-TGR23-2 ligand monoclonal antibody bound to the solid phase; a method which comprises adding the hybridoma culture supernatant to a solid phase adsorbed with an anti-immunoglobulin antibody or Protein A, adding the TGR23-2 ligand labeled with a radioactive substance, an enzyme, etc. and detecting the TGR23-2 ligand monoclonal antibodies bound to the solid phase; etc. Screening and plating of the anti-TGR23-2 ligand monoclonal antibodies can be performed generally in a medium for animal cells (e.g., RPMI 1640) containing 10-20% fetal calf serum and supplemented with HAT (hypoxanthine, aminopterin and thymidine). The antibody titer in the hybridomas culture supernatant can be assayed as in the assay for the antibody titer in the antisera with the anti-TGR23-2 ligand described above.

Separation and purification of the anti-TGR23-2 ligand monoclonal antibody can be carried out by methods applied to conventional separation and purification of immunoglobulins, as in the conventional methods for separation and purification of polyclonal antibodies [e.g., salting-out, alcohol precipitation, isoelectric point precipitation, electrophoresis, adsorption and desorption with ion exchangers (e.g., DEAE), ultracentrifugation, gel filtration, or a specific purification method which involves collecting only an antibody with an activated adsorbent such as a antigen-binding solid phase, Protein A, Protein G, etc. and dissociating the binding to obtain the antibody; and the like].

As described above, the antibody of the present invention can be produced by culturing hybridoma cells in a warm-blooded animal in vivo or in vitro and collecting the antibody from the body fluids or culture medium.

Hybridomas that produce the anti-TGR23-2 ligand antibody reacting with a segment (partial region) of the TGR23-2 ligand and hybridomas that produce the anti-TGR23-2 ligand monoclonal antibody reacting with the TGR23-2 ligand but not reacting with its segment (partial region) can be screened, for example, by measuring the binding property of a peptide corresponding to the segment to an antibody produced by the hybridoma.

[1] Method of Quantifying the TGR23-2 Ligand Using the Antibody of the Present Invention, Diagnosis for Cancer, etc.

Hereinafter, the method of quantifying the TGR23-2 ligand (immunoassay) is described in more detail.

Using the antibody of the present invention, the TGR23-2 ligand can be assayed and can also be detected by tissue staining, or the like. For these purposes, the antibody molecule itself may be used, or F(ab')2, Fab' or Fab fractions of the antibody molecule may be used.

The quantification method using the antibody of the present invention is not particularly limited. Any quantification method can be used, so long as the amount of antibody, antigen or antibody-antigen complex corresponding to the amount of antigen (e.g., the level of TGR23-2 ligand) in a fluid to be tested can be detected by chemical or physical means and the amount of the antigen can be calculated from a standard curve prepared from standard solutions containing known amounts of the antigen. For such an assay method, for example, the sandwich assay, the competitive assay, the immunometric method, nephrometry, etc. are used, and the sandwich assay and the competitive assay described below are more preferred in terms of sensitivity and specificity, with the sandwich assay being particularly preferable.

(1) Sandwich Assay

After the antibody of the present invention immobilized on a carrier is reacted with a labeled form of the antibody of the present invention and a fluid to be tested, the activity of a marker is assayed to quantify the TGR23-2 ligand in the test fluid.

Preferably, the sandwich assay includes:

(i) A method for quantification of the TGR23-2 ligand in a test fluid, which comprises reacting the antibody specifically reacting with a partial peptide in the N-terminal region of the TGR23-2 ligand immobilized onto a carrier, a labeled form of the antibody specifically reacting with a partial peptide in the C-terminal region (C-terminal region of the polypeptide comprising the amino acid sequence represented by SEQ ID NO: 2 or SEQ ID NO: 3, or a salt thereof) and the test fluid, and assaying the activity of a marker;

(ii) A method for quantification of the TGR23-2 ligand in a test fluid, which comprises reacting the antibody specifically reacting with a partial peptide in the C-terminal region (C-terminal region of the polypeptide comprising the amino acid sequence represented by SEQ ID NO: 2 or SEQ ID NO: 3, or a salt thereof) of the TGR23-2 ligand immobilized onto a carrier, the antibody specifically reacting with a partial peptide in the N-terminal region of a labeled form of the TGR23-2 ligand and the test fluid, and assaying the activity of a marker; etc.

A more preferred technique of the sandwich assay includes a method for quantification, wherein the antibody specifically reacting with a partial peptide in the N-terminal region of the TGR23-2 ligand is a monoclonal antibody represented by 23L-1Na, and the antibody specifically reacting with a partial peptide in the C-terminal region of the TGR23-2 ligand is a monoclonal antibody represented by 23L-2Ca.

In the sandwich assay, the immobilized antibody of the present invention is reacted with a test fluid (primary reaction), then with a labeled form of antibody of the present invention (secondary reaction), and the activity of the labeling agent on the immobilizing carrier is assayed, whereby the TGR23-2 ligand level in the test fluid can be quantified. The primary and secondary reactions may be performed simultaneously or with some time intervals. The methods of labeling and immobilization can be performed by modifications of those methods described above. In the immunoassay by the sandwich assay; the antibody used for immobilized or labeled antibody is not necessarily from one species, but a mixture of two or more species of antibodies may be used to increase the measurement sensitivity, etc. In the method of assaying TGR23-2 ligand by the sandwich assay, for example, when the antibodies used in the primary reaction recognize the partial peptides in the C-terminal region of TGR23-2 ligand (the C-terminal region of the polypeptide comprising the amino acid sequence represented by SEQ ID NO: 2 or SEQ ID NO: 3, or a salt thereof), the antibodies used in the secondary reaction are preferably those recognizing partial peptides other than the C-terminal region (i.e., the N-terminal region). When the antibodies used for the primary reaction recognize partial peptides in the N-terminal region of TGR23-2 ligand, the antibodies used in the secondary reaction, antibodies recognizing partial peptides other than the N-terminal region (i.e., the C-terminal region) are preferably employed.

As specific examples of such antibodies, there are used the monoclonal antibody represented by 23L-1Na and the monoclonal antibody represented by 23L-2Ca. These antibodies are preferably used in a labeled form with horse radish peroxidase (HRP).

(2) Competitive Assay

The antibody of the present invention, a test fluid and a labeled form of the TGR23-2 ligand are competitively reacted and a ratio of the labeled TGR23-2 ligand bound to the antibody is measured, thereby to quantify the TGR23-2 ligand in the test fluid.

The competitive assay is performed by, e.g., a solid phase technique.

Specifically, anti-mouse IgG antibody (manufactured by ICN/CAPPEL) is used as a solid phase antibody, (i) the antibody of the present invention (e.g., 23L-1Na, 23L-2Ca, etc.), (ii) the TGR23-2 ligand labeled with HRP, and (iii) a test fluid are added to a plate where the solid phase antibody is present; after the reaction, the HRP activity adsorbed onto the solid phase is assayed to quantify the TGR23-2 ligand.

(3) Immunometric Assay

In the immunometric assay, an antigen in a test fluid and a solid phase antigen are competitively reacted with a given amount of a labeled form of the antibody of the present invention followed by separating the solid phase from the liquid phase; or an antigen in a test fluid and an excess amount of labeled form of the antibody of the present invention are reacted, then a solid phase antigen is added to bind an unreacted labeled form of the antibody of the present invention to the solid phase and the solid phase is then separated from the liquid phase. Thereafter, the labeled amount of any of the phases is measured to determine the antigen level in the test fluid.

(4) Nephrometry

In the nephrometry, the amount of insoluble sediment, which is produced as a result of the antigen-antibody reaction in a gel or in a solution, is measured. Even when the amount of an antigen in a test fluid is small and only a small amount of the sediment is obtained, a laser nephrometry utilizing laser scattering can be suitably used.

Examples of labeling agents, which are employed for the aforesaid assay methods (1) to (4) using labeling agents, include radioisotopes (e.g., [$^{125}$I], [$^{131}$I], [$^{3}$H], [$^{14}$C], [$^{32}$P], [$^{33}$P], [$^{35}$S], etc.), fluorescent substances [e.g., cyanine fluorescent dyes (e.g., Cy2, Cy3, Cy5, Cy5.5, Cy7 (manufactured by Amersham Biosciences), etc.), fluorescamine, fluorescein isothiocyanate, etc.], enzymes (e.g., β-galactosidase, β-glucosidase, alkaline phosphatase, peroxidase, malate dehydrogenase, etc.), luminescent substances (e.g., luminol, a luminol derivative, luciferin, lucigenin, etc.), biotin, lanthanides, etc. In addition, a biotin-avidin system may be used as well for binding an antibody to a labeling agent.

In the immobilization of antigens or antibodies, physical adsorption may be used. Alternatively, chemical binding that is conventionally used for immobilization of proteins, enzymes, etc. may be used as well. Examples of the carrier include insoluble polysaccharides such as agarose, dextran, cellulose, etc.; synthetic resins such as polystyrene, polyacrylamide, silicone, etc.; or glass; and the like.

In applying each of these immunoassay techniques to the method of the present invention, it is not necessary to set any special condition, operation, etc. The assay system of the present invention may be constructed in addition to the conditions or operations conventionally used for each of the assay techniques, taking into account the technical consideration of one skilled in the art. For details of such conventional technical means, reference may be made to a variety of reviews, reference books, etc. [for example, see Hiroshi Irie (ed.): "Radioimmunoassay" (published by Kodansha, 1974); Hiroshi Irie (ed.): "Radioimmunoassay; Second Series" (published by Kodansha, 1979); Eiji Ishikawa, et al. (ed.): "Enzyme Immunoassay" (published by Igaku Shoin, 1978); Eiji Ishikawa, et al. (ed.): "Enzyme Immunoassay" (Second Edition) (published by Igaku Shoin, 1982); Eiji Ishikawa, et al. (ed.): "Enzyme Immunoassay" (Third Edition) (published by Igaku Shoin, 1987); "Methods in Enzymology" Vol. 70 (Immunochemical Techniques (Part A)); ibid., Vol. 73 (Immunochemical Techniques (Part B)); ibid., Vol. 74 (Immunochemical Techniques (Part C)); ibid., Vol. 84 (Immunochemical Techniques (Part D: Selected Immunoassays)); ibid., Vol. 92 (Immunochemical Techniques (Part E: Monoclonal Antibodies and General Immunoassay Methods)); ibid., Vol. 121 (Immunochemical Techniques (Part I: Hybridoma Technology and Monoclonal Antibodies)] (all published by Academic Press); etc.). Thus, where the TGR23-2 ligand assay system of the present invention is constructed by applying the sandwich immunoassay method, its method is not limited to EXAMPLES later described.

Thus, the antibody of the present invention enables to quantify the TGR23-2 ligand with high sensitivity and is useful for clarification of the physiological functions of TGR23-2 ligand and for diagnosis of diseases associated with the TGR23-2 ligand. By determining the level of the TGR23-2 ligand contained in body fluids (e.g., blood, plasma, serum, urine, follicular fluid, spinal fluid, sperm, etc.) using the antibody of the present invention, a diagnosis can be made for diseases associated with the TGR23-2 ligand, for example, cancer (colorectal cancer, colon cancer, rectum cancer, breast cancer, lung cancer, non-small-cell lung cancer, prostate cancer, esophageal cancer, gastric cancer, liver cancer, biliary tract carcinoma, spleen cancer, renal cancer, bladder carcinoma, uterine cancer, ovarian cancer, cervical cancer, testicular cancer, thyroid cancer, pancreatic cancer, brain tumor, blood tumor, etc.), anorexia, hyperphagia, etc., or it is highly likely that one would suffer from these disease in the future.

For example, in diagnosis of colon cancer, the TGR23-2 ligand level in a body fluid is quantified and when the TGR23-2 ligand level is more abundant than in healthy volunteers, e.g., its blood level is about 100 fmol/ml or more, preferably about 150 fmol/ml or more, it is diagnosed that one suffers from colon cancer.

[2] Pharmaceutical Comprising the Antibody of the Present Invention

The antibody of the present invention can neutralize the activities of the TGR23-2 ligand (e.g., TGR23-binding activity, TGR23-cell stimulating activity, tumor growth activity, eating behavior suppressing activity, etc.) and thus, can be used as a safe pharmaceutical including an agent for the prevention/treatment of diseases associated with the TGR23-2 ligand, for example, cancers (e.g., colorectal cancer, colon cancer, rectal cancer, breast cancer, lung cancer, non-small cell lung cancer, prostate cancer, esophageal cancer, gastric cancer, liver cancer, biliary tract cancer, spleen cancer, kidney cancer, bladder cancer, uterine cancer, ovarian cancer, cervical cancer, testicular cancer, thyroid cancer, pancreatic cancer, brain tumor, blood tumor, etc.) or anorexia, etc., or as an eating (appetite) stimulant, and so on. Preferably, the antibody can be used as an agent for the preventing/treating cancers.

The antibody of the present invention may be administered in its intact form or in the form of an appropriate pharmaceutical composition. The pharmaceutical composition used for administration described above may contain the antibody of the present invention or its salt, a pharmacologically acceptable carrier and a diluent or an excipient. Such a pharmaceutical composition is provided in a dosage form suitable for oral or parenteral administration.

Examples of the composition for parenteral administration are injectable preparations, suppositories, etc. The injectable preparations may include dosage forms such as intravenous, subcutaneous, intracutaneous and intramuscular injections, drip infusions, etc. These injectable preparations may be prepared by methods publicly known. For example, the injectable preparations may be prepared by dissolving, suspending or emulsifying the antibody of the present invention or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate dissolution aid such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a dissolution aid such as benzyl benzoate, benzyl alcohol, etc. The injection thus prepared is preferably filled in an appropriate ampoule. The suppository used for rectal administration may be prepared by blending the aforesaid antibody or its salt with conventional bases for suppositories.

The composition for oral administration includes a solid or liquid dosage form, specifically, tablets (including dragees and film-coated tablets), pills, granules, powders, capsules (including soft capsules), syrups, emulsions, suspensions, etc. Such a composition is manufactured by publicly known methods and may contain carriers, diluents or excipients conventionally used in the field of pharmaceutical preparations. As the carriers and excipients for tablets e.g., lactose, starch, sucrose, magnesium stearate and the like are used.

Advantageously, the pharmaceutical compositions for oral or parenteral use described above are prepared into pharmaceutical preparations with a unit dose to fit a dose of the active ingredients. Such unit dose preparations include, for example, tablets, pills, capsules, injections (ampoules) and suppositories. The amount of the antibody contained is generally about 5 to about 500 mg per dosage unit form; it is preferred that the aforesaid antibody is contained in about 5 to about 100 mg especially in the form of injection, and in about 10 to 250 mg for the other forms.

Each of the compositions described above may further contain other active ingredients, unless any adverse interaction occurs due to blending with the antibody described above.

The therapeutic/preventive agent comprising the antibody of the present invention is safe and low toxic, and can be administered orally or parenterally to human or mammals (e.g., rats, rabbits, sheep, swine, bovine, cats, dogs, monkeys, etc.) as it is in the form of liquid preparations or as a pharmaceutical composition of appropriate dosage form.

The dose may vary depending on subject to be administered, target disease, symptoms, route for administration, etc. When used for the treatment of, e.g., colon cancer in an adult patient, it is advantageous that the antibody of the present invention is parenterally administered in a single dose of normally about 0.01 to 20 mg/kg body weight, preferably about 0.1 to 10 mg/kg body weight and more preferably about 0.1 to 5 mg/kg body weight about 1 to 5 times, preferably approximately 1 to 3 times a day. For oral administration, the corresponding dose may be administered. When symptoms are extremely serious, the dose may be increased depending on the conditions.

In the specification of the present invention, amino acids, etc. are shown by abbreviations and in this case, they are denoted in accordance with the IUPAC-IUB Commission on Biochemical Nomenclature or by the common codes in the art, examples of which are shown below. For amino acids that may have the optical isomer, L form is presented unless otherwise indicated.

Gly: glycine
Ala: alanine
Val: valine
Leu: leucine
Ile: isoleucine
Ser: serine
Thr: threonine
Cys: cysteine
Met: methionine
Glu: glutamic acid
Asp: aspartic acid
Lys: lysine
Arg: arginine
His: histidine
Phe: phenylalanine
Tyr tyrosine
Trp: tryptophan
Pro: proline
Asn: asparagine
Gln: glutamine
TFA: trifluoroacetic acid
DMF: N,N-dimethylformamide
SPDP: N-succinimidyl-3-(2-pyrimidyldithio)propionate
GMBS: N-(4-maleimidobutyryloxy)succinimide
BSA: bovine serum albumin
BTG: bovine thyroglobulin
EIA: enzyme immunoassay
HPLC: reverse phase high performance liquid chromatography
HRP: horseradish peroxidase
FBS: fetal bovine serum
d-FBS: dialyzed fetal bovine serum
TMB: 3,3',5,5'-tetramethylbenzidine
NMP: N-methylpyrrolidone
Boc: t-butyloxycarbonyl
Fmoc: 9-fluorenylmethyloxycarbonyl
DCC: N,N'-dichlorohexylcarbodiimide
Pbf: 2,2,4,6,7-pentamethyldihydrobenzofrane-5-sulfonyl
tBu: tertiary butyl
Trt: trityl
Tos: p-toluenesulfonyl
DIEA: N,N-diisopropylethylamine
HOBt: 1-hydroxybenzotriazole
HOAt: 1-hydroxy-7-azabenzotriazole
PyAop: 7-azabenzotriazol-1-yloxytrispirolydinophophonium hexafluorophosphate
Clt: 2-chlorotrityl
BHA: benzhydrylamine Thr($\Psi^{Me,Me}$Pro): 2,2-dimethyl-5-methyl-1,3-oxazolidine-4-carboxylic acid The sequence identification numbers used in the sequence listing of the specification represent the amino acid sequences of the following peptides.

[SEQ ID NO: 1]

This shows the amino acid sequence of human TGR23-2 ligand.

[SEQ ID NO: 2]

This shows the amino acid sequence of rat TGR23-2 ligand.

[SEQ ID NO: 3]

This shows the amino acid sequence of mouse TGR23-2 ligand.

[SEQ ID NO: 4]

This shows the amino acid sequence of [Cys$^{19}$] rat TGR23-2 ligand (1-19).

[SEQ ID NO: 5]

This shows the amino acid sequence of [Cys$^9$] rat TGR23-2, ligand (1-9).

The hybridoma cell obtained in EXAMPLE 1 later described, 23L-1N has been deposited on International Patent Organisms Depository, National Institute of Advanced Industrial Science and Technology, located at Central 6, 1-1-1 Higashi, Tsukuba, Ibaraki (postal code: 305-8566) under Accession Number FERM BP-8302 since Feb. 26, 2003.

The hybridoma cell obtained in EXAMPLE 1 later described, 23L-2C has been deposited on International Patent Organisms Depository, National Institute of Advanced Industrial Science and Technology, located at Central 6, 1-1-1 Higashi, Tsukuba, Ibaraki (postal code: 305-8566) under Accession Number FERM BP-8303 since Feb. 26, 2003.

The antibodies acquired from the respective hybridoma cells are shown by the cell names with suffix "a."

Hereinafter, the present invention will be described in more detail, with reference to EXAMPLES and REFERENCE EXAMPLES, but they are not deemed to limit the scope of the invention.

Hereinafter, 0.02M phosphate buffer (pH 7.0) containing 1% BSA, 0.4 M NaCl and 0.05% 2 mM EDTA.Na (ethylenediamine-N,N,N',N'-tetraacetic acid, disodium salt, dihydrate, DOJINDO Corp.) used below is referred to as Buffer C.

EXAMPLE 1

(1) Preparation of Immunogen Containing [Cys$^{19}$-NH$_2$] rat TGR23-2 Ligand (1-19)

A complex of [Cys$^{19}$-NH$_2$] rat TGR23-2 ligand (1-19) obtained in REFERENCE EXAMPLE 4 and keyhole limpet hemocyanin (KLH) was prepared and used as an immunogen.

That is, 20 mg of KLH was dissolved in 1.4 ml of 0.1 M phosphate buffer (pH 6.5) and the solution was mixed with 100 µl of DMF solution containing 2.2 mg (8 µmol) of N-(γ-maleimidobutyryloxy)succinimid (GMBS), followed by reacting at room temperature for 40 minutes. After the reaction, the reaction mixture was separated on a Sephadexm™ G-25 column. Next, 15 mg of maleimide-introduced KLH was mixed with 3.75mg of [Cys$^9$-NH2] rat TGR23-2 ligand (1-19). The resulting mixture was then reacted at 4° C. for a day. After the reaction, the mixture was dialyzed to physiological saline at 4° C. for 3 days.

(2) Immunization

The BALB/C female mice of 6 to 8 weeks old were primed subcutaneously with about 70 µg/animal of the [Cys$^{19}$-NH$_2$] rat TGR23-2 ligand (1-19)-KLH complex obtained (1) above in complete Freund's adjuvant. At 3-week intervals after the priming, mice were boosted twice or thrice with equal amounts of immunogen in incomplete Freund's adjuvant.

(3) Production of Horse Radish Peroxidase (HRP)-Labeled [Cys$^{19}$-NH$_2$] Rat TGR23-2 Ligand (1-19)

[Cys$^{19}$-NH$_2$] rat TGR23-2 ligand (1-19) was crosslinked with HRP (for enzyme immunoassay, manufactured by Boehringer Mannheim), which was used as a marker for enzyme immunoassay (EIA).

That is, 9.2 mg (180 nmol) of HRP was dissolved in 0.95 ml of 0.1 M phosphate buffer (pH 6.5) and the solution was mixed with 50 µl of DMF solution containing 0.504mg (1.8 µmol) of GMBS. After reacting at room temperature for 30 minutes, the reaction mixture was separated on a Sephadex™ G-25 column. Then, 6.4 mg (126 nmol) of the maleimide-introduced HRP thus prepared was mixed with 0.35 mg (378 nmol) of the [Cys$^{19}$-NH$_2$] rat T0R23-2 ligand (1-19) obtained in REFERENCE EXAMPLE 4. The mixture was reacted at 4° C. for a day. After the reaction, fractionation was performed on Ultrogel™ AcA44 (manufactured by LKB-Pharmacia) column to give HRP-labeled [Cys$^{19}$-NH$_2$] rat TGR23-2 ligand (1-19).

(4) Assay for Antibody Titer of Antisera in Mice Immunized with the [Cys$^{19}$-NH$_2$] Rat TGR23-2 Ligand (1-19)-KLH Complex Mice were immunized twice with the [Cys$^{19}$-NH$_2$] rat TGR23-2 ligand (1-19)-KLH complex at 3-week intervals. One week after, blood was drawn from the ocular fundus to collect blood. After the blood was further centrifuged at 4° C. for 15 minutes at 12,000 rpm, the supernatant was recovered to give antisera. The antibody titer in antisera was assayed by the following method. To prepare an anti-mouse immunoglobulin antibody-bound microplate, 100 µl each of 0.1M carbonate buffer (pH 9.6) solution containing 100 µg/ml of anti-mouse immunoglobulin antibody (IgG fraction, manufactured by Cappel) was first dispensed onto a 96-well microplate and then-allowed to stand at 4° C. over 24 hours. Next, after the plate was washed with phosphate buffered saline (PBS, pH 7.4), a 300 µl aliquot of PBS containing 25% Block Ace (manufactured by Snow Brand Milk Products) was dispensed in each well and treated at 4° C. for at least 24 hours to block redundant binding sites of the well.

After 50 µl of Buffer C and 100 µl of antisera to the complex diluted with Buffer C were added to each well of the obtained anti-mouse immunoglobulin antibody-bound microplate, the reaction was carried out at 4° C. for 16 hours. Next, the plate was washed with PBS and 100 µl of HRP-labeled [Cys$^{19}$-NH$_2$] rat TGR23-2 ligand (1-19) (diluted to 400-fold with Buffer C) prepared in (3) above was added thereto, followed by reacting at room temperature for a day. The plate was then washed with PBS and 100 µl of TMB (3,3',5,5'-tetramethylbenzidine) Microwell Peroxidase Substrate System (KIRKEGAARD & PERRY LAB, INC., consigned to Funakoshi Co., Ltd.) was added thereto and the reaction was carried out at room temperature for 10 minutes to assay the enzyme activity on a solid phase. The reaction was terminated by adding 100 µl of 1M phosphoric acid.

Absorption at 450 nm was measured with a plate reader (BICHROMATIC, manufactured by Dainippon Pharmaceutical Co., Ltd.).

The results are shown in FIG. 1. Increased antibody titers to [$Cys^{19}$-$NH_2$] rat TGR23-2 ligand (1-19) were observed in the antisera with 6 out of the 8 immunized mice.

(5) Production of Anti-TGR23-2 Ligand Monoclonal Antibodies

Mice showing relatively high antibody titers received final immunization by intravenous injection with solutions of 50 µg of the immunogen in 0.2 ml of saline. After 4 days of the final immunization, the spleen was removed from the mice, and the spleen was pressed against a stainless mesh and filtered through the stainless mesh. Spleen cells were suspended in Eagles' minimum essential medium (MEM) to give the spleen cell suspension. BALB/C mouse-derived myeloma cells P3-X63.Ag8.U1 (P3U1) were used as cells for cell fusion (Current Topics in Microbiology and Immunology, 81, 1, 1978).

The cell fusion was performed by the original method (Nature, 256, 495, 1975) with modifications.

The spleen cells and P3U1 were washed 3 times with serum-free MEM, respectively, and they were blended in a 5:1 proportion of the spleen cells to P3U1 in cell count. The cell mixture was centrifuged at 800 rpm for 15 minutes to deposit the cells. After the supernatant was thoroughly removed, the deposit was lightly unraveled and 0.3 ml of 45% polyethylene glycol (PEG) 6000 (manufactured by Kochlight) was added thereto. The mixture was allowed to stand for 7 minutes in a warm water bath of 37° C. to perform cell fusion. The fusion was followed by addition of MEM to the cells at a rate of 2 ml/min. After 15 ml of MEM in total was added, the mixture was centrifuged at 600 rpm for 15 minutes and the supernatant was removed. The cell deposit was suspended in 10% fetal calf serum-containing GIT medium (Wako Pure Chemical Industries, Ltd.) (GIT-10% FCS) in $2 \times 10^5$/ml of P3U1, and the suspension was plated on 192 wells of a 24-well Multidish (manufactured by Limbro) in 1 ml/well. After the plating, the cells were incubated at 37° C. in a 5% carbonic acid gas incubator. Twenty-four hours after, GIT-10% FCS medium containing HAT ($1 \times 10^{-4}$ M hypoxanthine, $4 \times 10^{-7}$ M aminopterin, $1.6 \times 10^{-3}$ M thymidine) (HAT medium) was added to the cells in 1 ml/well, thereby to initiate HAT selective culture. The HAT selective culture was continued by discarding 1 ml of the old medium on Days 3, 6 and 9 after start of the incubation and replenishing 1 ml of HAT medium. Growth of hybridomas was noted in 9 to 14 days after the cell fusion. When the culture medium turned yellow (about $1 \times 10^6$ cells/ml), the supernatant was collected and the antibody titer was assayed in accordance with the procedure described in (4) above.

Figure 2:
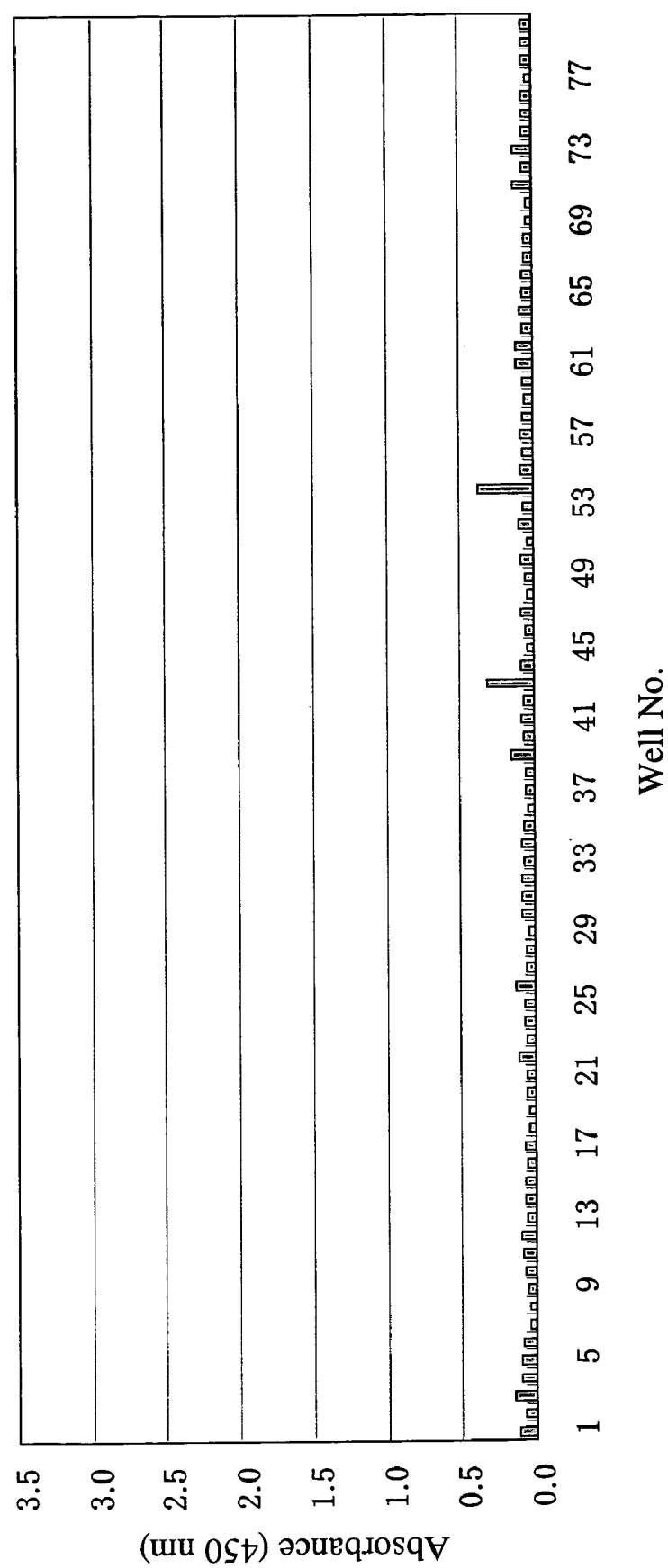
FIG. 2 shows the conditions in which hybridomas derived from mice immunized with the [$Cys^{19}$-$NH_2$] rat TGR23-2 ligand (1-19)-BTG complex produced antibodies (results of absorption spectrometry).
Figure 3:
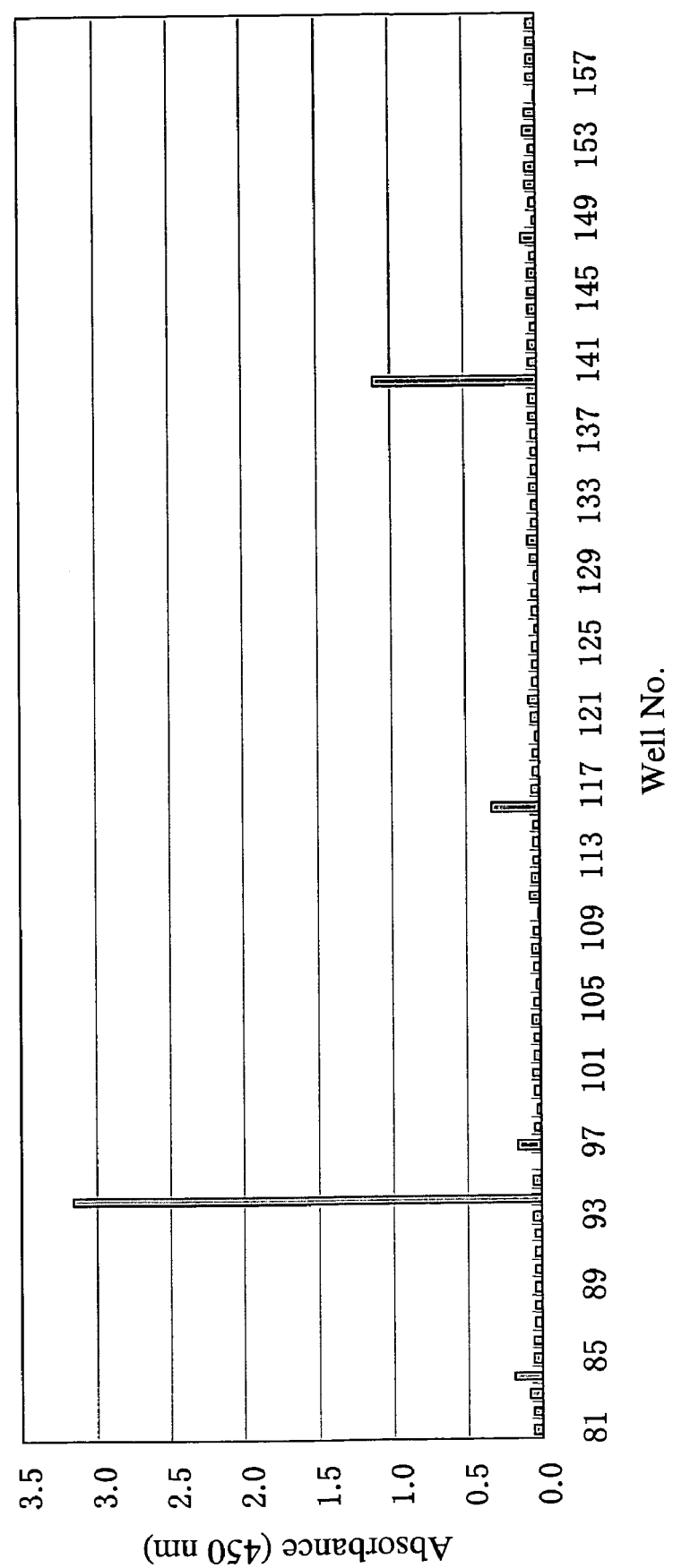
FIG. 3 shows the conditions in which hybridomas derived from mice immunized with the [$Cys^{19}$-$NH_2$] rat TGR23-2 ligand (1-19)-BTG complex produced antibodies (results of absorption spectrometry).
Figure 4:
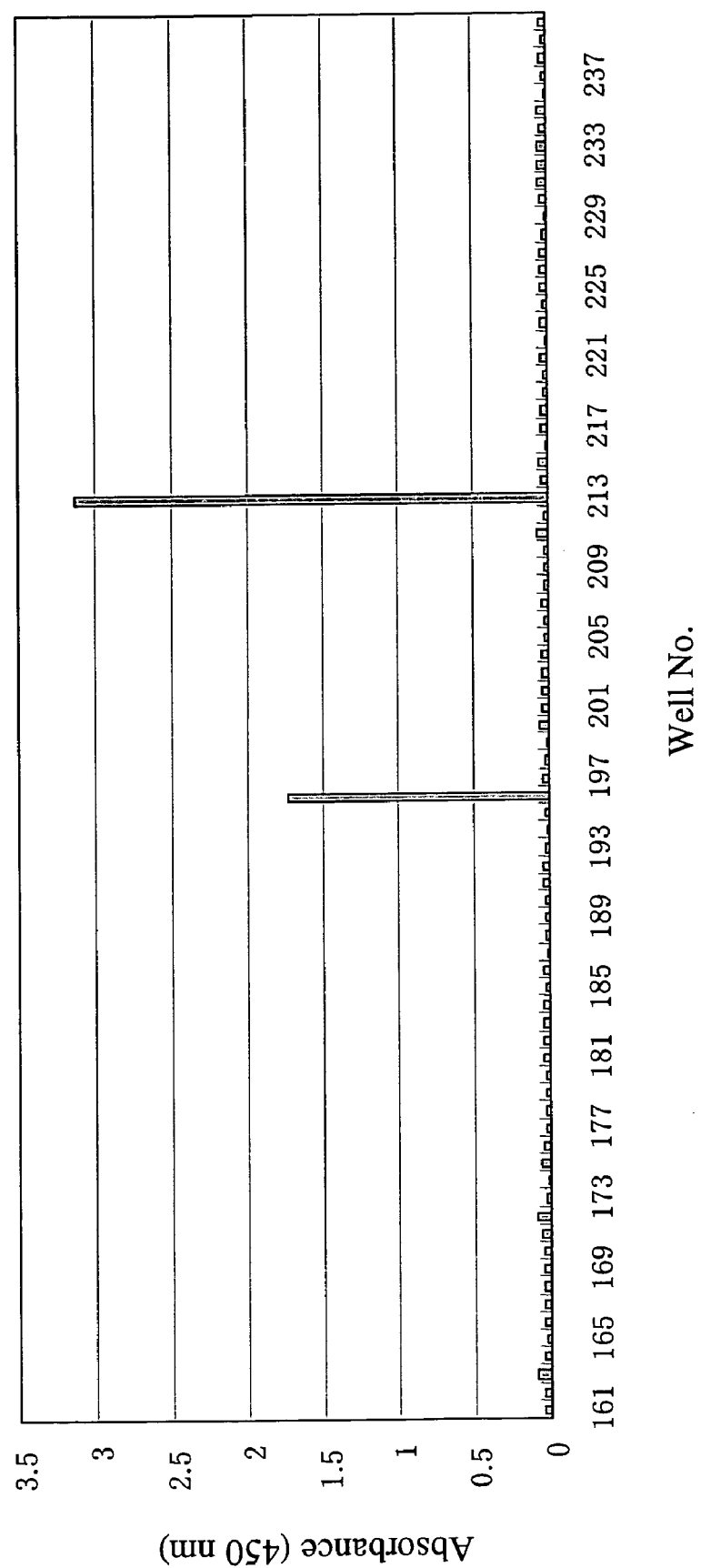
FIG. 4 shows the conditions in which hybridomas derived from mice immunized with the [$Cys^{19}$-$NH_2$] rat TGR23-2 ligand (1-19)-BTG complex produced antibodies (results of absorption spectrometry).

By way of examples of the selected antibody-producing cell lines of the hybridomas derived from mice immunized with the [$Cys^{19}$-$NH_2$] rat TGR23-2 ligand (1-19)-KLH complex, the conditions of antibody production of hybridomas, which were obtained by cell fusion using mice No. 2 and No. 6 (see FIG. 1), are shown in FIGS. 2 to 4. Total 3 hybridomas listed in Table 1 were selected from the antibody-producing hybridomas acquired.

TABLE 1

| Hybridoma No. | Reactivity[*] | | | | Antibody |
| | Human TGR23-2 ligand | Rat TGR23-2 ligand | Mouse TGR23-2 ligand | [$Cys^9$] rat TGR23-2 ligand (1-9) | |
| --- | --- | --- | --- | --- | --- |
| 1 | + | + | + | + | 23L-1Na |
| 2 | − | + | − | − | 23L-1Ca |
| 3 | − | + | + | − | 23L-2Ca |

[*]When 100 nM of each TGR23-2 ligand was present:
+: ($B/B_0$) ≦ 0.50
−: 0.50 < ($B/B_0$)
B: Amount of HRP-labeled rat TGR23-2 ligand bound to the antibody in the presence of antigen
$B_0$: Amount of HRP-labeled rat TGR23-2 ligand bound to the antibody in the absence of antigen Next, these hybridomas obtained above were cloned by the limiting dilution. In cloning, thymocytes from BALB/C mice were added as feeder cells in $5 \times 10^5$ cells/well. After cloning, the hybridomas were intraperitoneally injected to mice (BALB/C) in 1 to $3 \times 10^6$ cells/mouse, to which 0.5 ml of mineral oil had previously been given intraperitoneally. The ascites fluid containing the antibody was collected 6 to 20 days after.

The monoclonal antibody was purified through protein A column from the ascites fluid obtained. After 6 to 20 ml of the ascites fluid was diluted with an equal volume of binding buffer [1.5M glycine containing 3.5M NaCl and 0.05% $NaN_3$ (pH 9.0)], the dilution was applied on recombinant protein A-agarose (manufactured by Repligen Corporation) column, which had been previously equilibrated with the binding buffer. The specific antibody was eluted with an eluting buffer [0.1M citrate buffer containing 0.05% $NaN_3$ (pH 3.0)]. After the eluate was dialyzed to PBS at 4° C. for 2 days, which was subjected to cell-free filtration through a filter of 0.22 µm (manufactured by Millipore) and then stored at 4° C. or −80° C.

In class/subclass determinations of the monoclonal antibodies, enzyme-linked immunosorbent assay (ELISA) using purified monoclonal antibody-bound solid phase was carried out. That is, 100 µl each of 0.1M carbonate buffer (pH 9.6) solution containing 2 µg/ml of the antibody was dispensed on a 96-well microplate, which was then allowed to stand at 4° C. for 24 hours. Following the procedure described above, redundant binding sites in the wells were blocked with Block Ace in accordance with the procedure described in (1) above. Thereafter, the class and subclass of immobilized antibodies were determined by ELISA using an isotyping kit (Mouse-Typer™ Sub-Isotyping Kit, manufactured by BioRAD). In all of three monoclonal antibodies examined, the H chain was IgG1 and the L chain was κ.

EXAMPLE 2

Study of Recognition Sites for Antibodies by Competitive Enzyme Immunoassay

The monoclonal antibodies prepared using the [$Cys^{19}$-$NH_2$] rat TGR23-2 ligand (1-19)-KLH complex as an immunogen were examined for their reaction specificity according to the following method.

First, the antibody titers of respective solutions of the three monoclonal antibodies obtained were assayed by the method described in EXAMPLE 1-(4) above, and the antibody level wherein the binding amount of a labeled form reached about 50% of the saturation binding amount was determined as an antibody level used for the competitive assay-EIA (about 10 to 50 ng/ml). Next, to the anti-mouse immunoglobulin antibody-bound microplate described in EXAMPLE 1-(4) above, (i) 50 μl of anti-rat TGR23-2 ligand (1-19) antibody solution diluted with Buffer C in 50 ng/ml for 23L-1Na, 10 ng/ml for 23L-1Ca, or 30 ng/ml for 23L-2Ca, (ii) 50 μl of human TGR23-2 ligand solution, 50 μl of rat TGR23-2 ligand solution, 50 μL of mouse TGR23-2 ligand solution or 50 μl of [$Cys^9$-$NH_2$] rat TGR23-2 ligand (1-9) solution (EXAMPLE 8 described later), which was diluted with Buffer C, and (iii) 50 μl of HRP-labeled [$Cys^{19}$-$NH_2$] rat TGR23-2 ligand (1-19) (diluted to 250-fold with Buffer C) obtained in EXAMPLE 1-(3) were added, followed by reaction at 4° C. for 16 hours. After the reaction, the plate was washed with PBS and the enzyme activity on the anti-mouse immunoglobulin antibody-bound microplate was assayed by the method described in EXAMPLE 1-(4) above.

The results are shown in Table 1. Based on the results, the recognition sites of these three antibodies were considered as follows.

It is noted that 23L-1Na is reactive with human TGR23-2 ligand, rat TGR23-2 ligand and mouse TGR23-2 ligand and further reactive with [$Cys^9$-$NH_2$] rat TGR23-2 ligand (1-9). Therefore, the recognition site for 23L-1Na is considered to be human TGR23-2 ligand (1-7), which is a motif of these peptides (the 1st-7th amino acid sequence in the amino acid sequences represented by SEQ ID NO: 1, SEQ ID NO: 2 and SEQ ID NO: 3).

23L-1Ca is reactive with rat TGR23-2 ligand but not reactive with human TGR23-2 ligand, mouse TGR23-2 ligand or [$Cys^9$-$NH_2$] rat TGR23-2 ligand (1-9). Therefore, the recognition site for 23L-1Ca is considered to be rat TGR23-2 ligand (9-12) centering on valine at position 10 (the 9th-12th amino acid sequence in the amino acid sequence represented by SEQ ID NO: 2).

23L-2Ca is reactive with rat TGR23-2 ligand and mouse TGR23-2 ligand but not reactive with human TGR23-2 ligand and [$Cys^9$-$NH_2$] rat TGR23-2 ligand (1-9). Therefore, the recognition site for 23L-2Ca is considered to be rat-TGR23-2 ligand (15-18) and mouse TGR23-2 ligand (15-18) centering on arginine at position 16 (the 15th-18th amino acid sequence in the amino acid sequences represented by SEQ ID NO: 2 and SEQ ID NO: 3).

Figure 5:
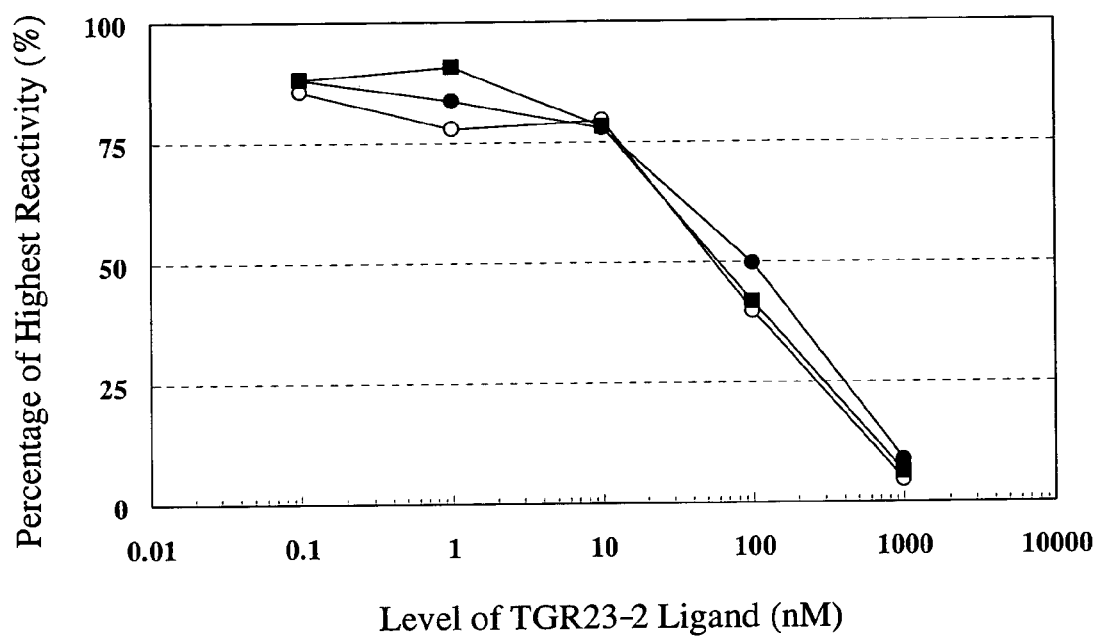
FIG. 5 shows the results of 23L-1Na by the competitive assay-EIA. In the figure, -●-(-closed circle-) represents the reactivity with human TGR23-2 ligand, -○-(-open circle-) represents the reactivity with rat TGR23-2 ligand, and -■-(-closed square-) represents the reactivity with mouse TGR23-2 ligand.
Figure 6:
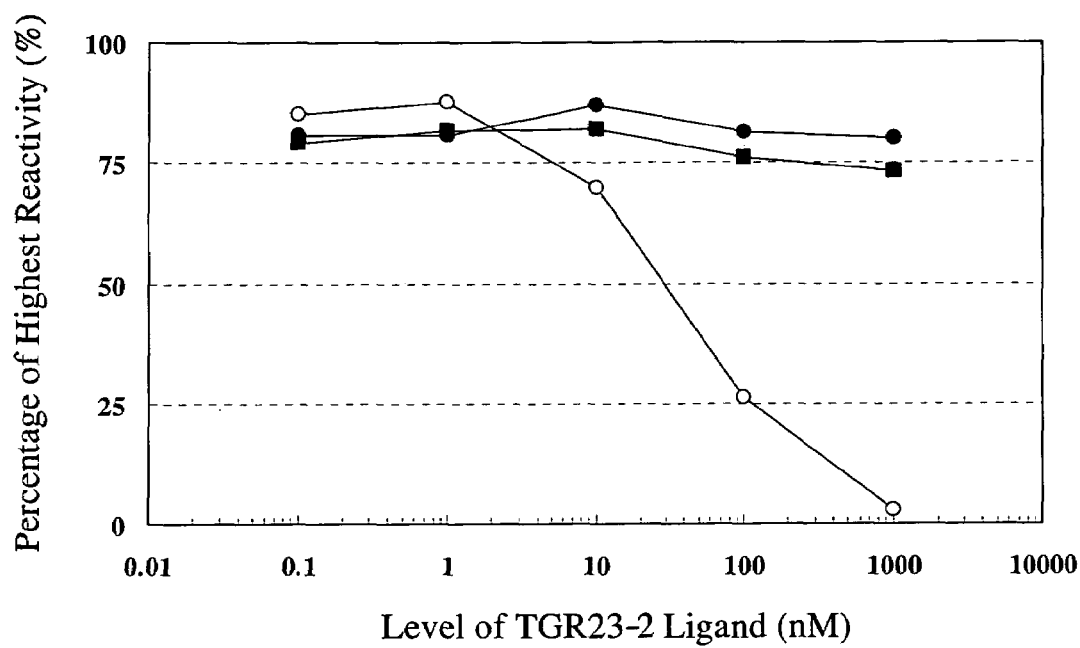
FIG. 6 shows the results of 23L-1Ca by the competitive assay-EIA. In the figure, -●-(-closed circle-) represents the reactivity with human TGR23-2 ligand, -○-(-open circle-) represents the reactivity with rat TGR23-2 ligand, and -■-(-closed square-) represents the reactivity with mouse TGR23-2 ligand.
Figure 7:
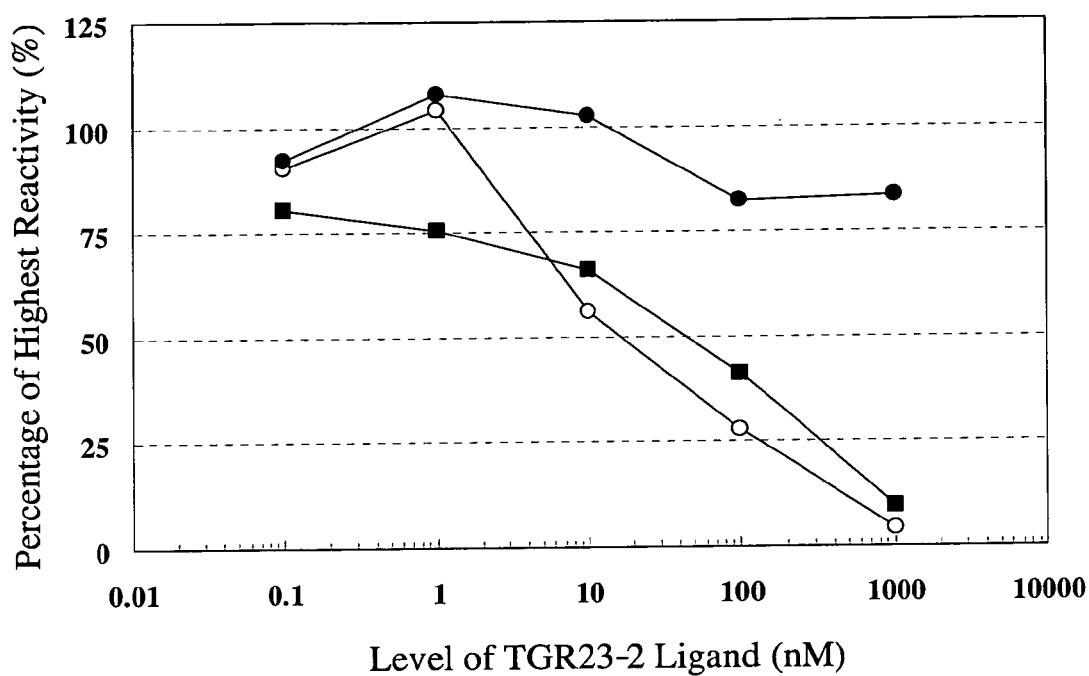
FIG. 7 shows the results of 23L-2Ca by the competitive assay-EIA. In the figure, -●-(-closed circle-) represents the reactivity with human TGR23-2 ligand, -○-(-open circle-) represents the reactivity with rat TGR23-2 ligand, and -■-(-closed square-) represents the reactivity with mouse TGR23-2 ligand.

Next, the results of the monoclonal antibodies by the competitive assay-EIA are shown in FIGS. 5, 6 and 7, respectively, by way of illustration.

From the standard curves of 23L-1Na for human TGR23-2 ligand, rat TGR23-2 ligand and mouse TGR23-2 ligand, it is noted that the levels providing the ratio of 0.5 to the highest reactivity ($B/B_0$) were 60 nM in human TGR23-2 ligand and mouse TGR23-2 ligand and 100 nM in rat TGR23-2 ligand (FIG. 5). These results suggest that 23L-1Na shows high reactivities with all of human TGR23-2 ligand, rat TGR23-2 ligand and mouse TGR23-2 ligand.

From the standard curves of 23L-1Ca for human TGR23-2 ligand, rat TGR23-2 ligand and mouse TGR23-2 ligand, it is noted that the level providing the ratio of 0.5 to the highest reactivity ($B/B_0$) was 20 nM in rat TGR23-2 ligand but 23L-1Ca does not react with human TGR23-2 ligand and mouse TGR23-2 ligand (FIG. 6). These results suggest that 23L-1Ca shows high reactivity only with rat TGR23-2 ligand.

From the standard curves of 23L-2Ca for human TGR23-2 ligand, rat TGR23-2 ligand and mouse TGR23-2 ligand, it is noted that the levels providing the ratio of 0.5 to the highest reactivity ($B/B_0$) were 20 nM in rat TGR23-2 ligand and 40 nM in mouse TGR23-2 ligand but 23L-2Ca does not react with human TGR23-2 ligand (FIG. 7). These results suggest that 23L-2Ca shows high reactivities only with rat TGR23-2 ligand and mouse TGR23-2 ligand.

EXAMPLE 3

Preparation of HRP-Labeled Anti-TGR23-2 Ligand Monoclonal Antibody (23L-2Ca-HRP)

After 50 μl of DMF containing 0.59 μmol of GMBS was added to 0.1M phosphate buffer (pH 6.8) containing 8.91 mg (59.4 nmol) of the purified fraction of 23L-2Ca, the mixture was reacted at room temperature for 40 minutes. The reaction liquid was separated on a Sephadex G-25 column (eluent: 0.1M phosphate buffer, pH 6.7) to give 6.23 mg of the maleimide-introduced antibody fraction. Next, 60 μl of DMF containing 6.42 μmol of SPDP was added to 1.14 ml of 0.02M phosphate buffer (pH 6.8) containing 17.1 mg (428 nmol) of HRP (further containing 0.15M NaCl), and the mixture was reacted at room temperature for 40 minutes. Subsequently, 0.4 ml of 0.1M acetate buffer (pH 4.5) containing 64.2 μmol of dithiothreitol was added to the mixture. After reacting at room temperature for 20 minutes, the reaction mixture was separated on a Sephadex G-25 column (Eluent: 0.1M phosphate buffer containing 2 mM EDTA, pH 6.0) to give 9.2 mg of SH-introduced HRP. Next, 8 mg of the SH-introduced HRP was mixed with 3 mg of the maleimide-introduced antibody fraction. After the mixture was concentrated to about 0.5 ml with Collodion Bag (manufactured by Sartorius K.K.), the concentrate was allowed to stand at 4° C. for 16 hours. The reaction liquid was applied to a Sephacryl S-300HR column (manufactured by Pharmacia), which had been equilibrated with 0.1 M phosphate buffer (pH 6.5), to purify the 23L-2Ca-HRP complex fraction.

EXAMPLE 4

Sandwich Assay-EIA

After 100 μl each of 0.1M carbonate buffer (pH 9.6 solution) containing 15 μg/ml of the purified monoclonal antibody 23L-1Na obtained in EXAMPLE 1 was dispensed in a 96-well microplate, the plate was allowed to stand at 4° C. for 24 hours. The redundant binding sites in the wells were inactivated by adding 400 μl of Block Ace diluted with PBS to 4-fold.

To the plate prepared as above, 100 μl each of human TGR23-2 ligand, rat TGR23-2 ligand or mouse TGR23-2 ligand standard solutions diluted in Buffer C was added, and the mixture was reacted at 4° C. for 24 hours. After washing with PBS, 100 μl of 23L-2Ca-HRP (diluted with Buffer C to 3,000-fold) prepared in EXAMPLE 3 above was added to the reaction mixture, followed by reacting at 4° C. for 24 hours. After washing with PBS, the enzyme activity on the solid phase was assayed in accordance with the procedure described in EXAMPLE 1-(4) above, using the TMB microwell peroxidase substrate system (enzyme reaction for 30 minutes).

Figure 8:
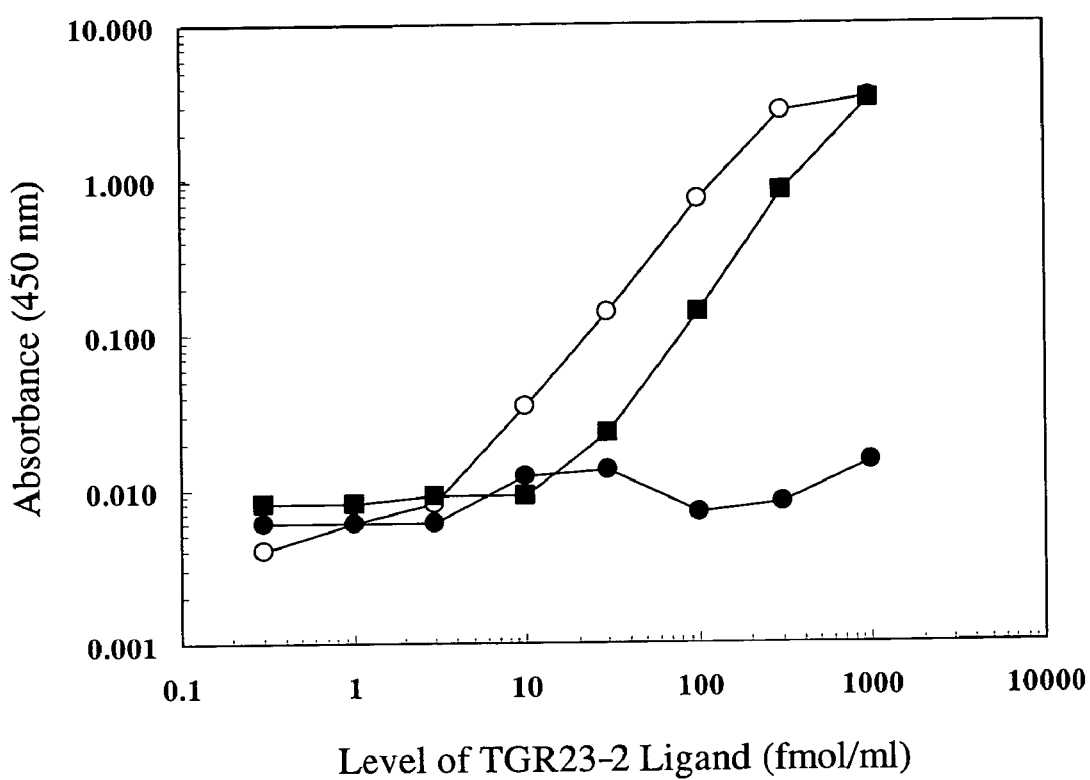
FIG. 8 shows the results of the sandwich assay-EIA using 23L-1Na and 23L-2Ca-HRP. In the figure, -●-(-closed circle-) represents the reactivity with human TGR23-2 ligand, -○-(-open circle-) represents the reactivity with rat TGR23-2 ligand, and -■-(-closed square-) represents the reactivity with mouse TGR23-2 ligand.

The results are shown in FIG. 8.

According to this sandwich assay-EIA, rat TGR23-2 ligand and mouse TGR23-2 ligand could be detected in 3 fmol/ml and 10 fmol/ml, respectively, and any reaction with human TGR23-2 ligand did not occur to the level of 1000 fmol/mL. It is thus noted that the sandwich assay-EIA using 23L-1Na as a solid phase and 23L-2Ca-HRP as a marker enables to detect rat TGR23-2 ligand and mouse TGR23-2 ligand with extremely high sensitivity and selectivity.

EXAMPLE 5

Neutralizing Action on the Biological Activity of Mouse TGR23-2 Ligand by 23L-1Na and 23L-2Ca The neutralizing action on mouse TGR23-2 ligand by 23L-1Na and 23L-2Ca was determined on FLIPR (Molecular Devices, Co.) using the TGR23-2-expressed CHO cells described in REFERENCE EXAMPLE 1 in WO 02/31145, where the intracellular $Ca^{2+}$ ion level-increasing activity was used as an indicator.

The TGR23-2-expressed CHO cells were suspended in Dulbecco's modified Eagle medium (DMEM) (Nissui Seiyaku Co., Ltd.) supplemented with dialyzed fetal bovine serum (hereinafter dFBS) (JRH BIOSCIENCES, Inc.) (10% dFBS-DMEM) in $3 \times 10^4$ cells/ml. Using a dispenser, 200 μl each of the suspension was inoculated on a 96-well plate for FLIPR (Black plate clear bottom, Coster, Inc.) ($4 \times 10^4$ cells/ 200 μl/well), followed by incubation at 37° C. overnight in a 5% $CO_2$ incubator. The cells thus incubated were used (hereinafter referred to as the cell plate). Subsequently, 20 ml of FLIPR assay buffer [9.8 g of Nissui HANKS 2 (Nissui Seiyaku Co., Ltd.), 0.35 g of sodium hydrogencarbonate, 4.77 g of HEPES; after adjusting the pH to 7.4 with 6M sodium hydroxide solution, the volume was made 1 L followed by sterilization through a filter], 200 μl of 250 mM Probenecid (SIGMA) and 210 μl of fetal bovine serum (FBS) were mixed. Furthermore, 2 vials (50 μg) of Fluo 3-AM (Dojin Chemical Laboratory, Ltd.) were dissolved in 40 μl of dimethylsulfoxide and 40 μl of 20% Pluronic acid (Molecular Probes, Inc.). The resulting solution was added to H/HBSS-Probenecid-FBS solution composed of 20 ml of H/HBSS [9.8 g of HEPES buffered HANKS' balanced solution (Nissui HANKS 2 (Nissui Seiyaku Co., Ltd.), 0.35 g of sodium hydrogencarbonate, 4.77 g of HEPES; after adjusting the pH to 7.4 with sodium hydroxide solution, followed by sterilization through a filter], 200 μl of 250 mM Probenecid and 200 μl of FBS and then mixed therewith. After the culture solution was removed using an 8-channel pipette, 100 μl each/well of the mixture was dispensed to the culture medium-removed cell plate, followed by incubation at 37° C. for an hour in a 5% $CO_2$ incubator (dye loading). 23L-1Na and 23L-2Ca were diluted in 120 μl of Hanks'/HBSS containing 2.5 mM Probenecid and 0.2% BSA. After incubation with mouse TGR23-2 ligand ($5.0 \times 10^{10}$M) at 37° C. for an hour, 5 μl of each fraction was transferred to a 96-well plate for FLIPR (V-Bottom Plate, Coster, Inc.) (hereinafter referred to as a sample plate). After completion of the dye loading onto the cell plate, the cell plate was washed 4 times with a wash buffer, which was obtained by adding 2.5 mM Probenecid to Hanks'/HBSS, using a plate washer (Molecular Devices, Co.) to leave 100 μl of the wash buffer after the washing. The cell plate and the sample plate were set in FLIPR for the assay (50 μl of a sample from the sample plate was automatically transferred to the cell plate on the FLIPR device).

Figure 9:
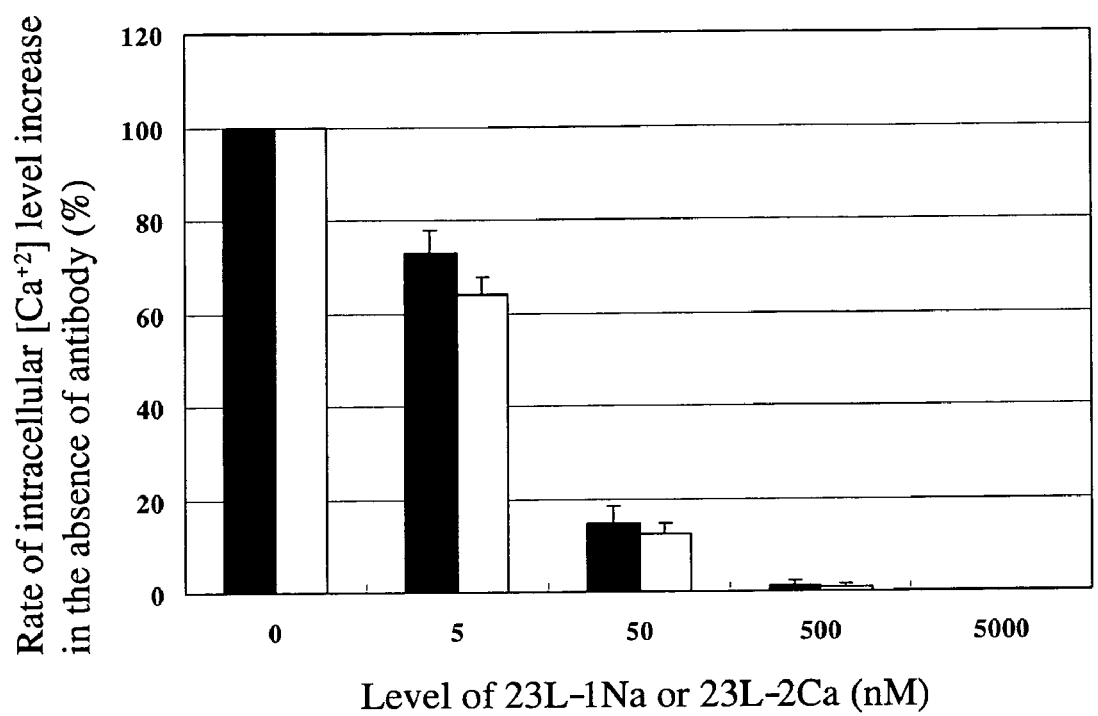
FIG. 9 shows the neutralizing action of mouse TGR23-2 ligand in the co-presence of 23L-1Na or 23L-2Ca on the intracellular $Ca^{2+}$ ion level increasing activity using the TGR23-2-expressed CHO cells. The intracellular $Ca^{2+}$ ion level increasing activity is shown after mouse TGR23-2 ligand ($5 \times 10^{-10}$ M) was reacted with 23L-1Na or 23L-2Ca at room temperature for an hour in each ratio of 1:1, 1:10, 1:100 or 1:1000. In the figure, solid bars and open bars represent the percentage of control (without adding any antibody) for the intracellular $Ca^{2+}$ ion level increasing activity in the TGR23-2-expressed CHO cells, when 23L-1Na and 23L-2Ca were co-present with mouse TGR23-2 ligand, respectively.

The results are shown in FIG. 9.

The results reveal that 23L-1Na suppressed the activity of mouse TGR23-2 ligand ($5.0 \times 10^{-10}$ M) up to about 74% at $5 \times 10^{-9}$ M higher by 10-fold molar concentration and up to about 15% at $5 \times 10^{-8}$ M higher by 100-fold molar concentration. The results further reveal that 23L-2Ca suppressed the activity of mouse TGR23-2 ligand ($5.0 \times 10^{-10}$ M) up to about 65% at $5 \times 10^{-9}$ M higher by 10-fold molar concentration and up to about 12% at $5 \times 10^{-8}$ M higher by 100-fold molar concentration.

From the foregoing results, it has become clear that 23L-1Na and 23L-2Ca neutralize the intracellular $Ca^{2+}$ ion level-increasing activity of mouse TGR23-2 ligand, indicating that these antibodies are usable as neutralizing antibodies to mouse TGR23-2 ligand.

EXAMPLE 6

Quantification of Mouse TGR23-2 Ligand in Plasma

Male Balb/C mouse (6 weeks old) plasma was diluted to 2-fold with an equal volume of Buffer C and mouse TGR23-2 ligand was quantified by the sandwich assay-EIA described in EXAMPLE 4 above.

The results are shown in Table 2.

TABLE 2

| No. | Immunological Activity of TGR23-2 ligand in mouse plasma (fmol/ml) |
|---|---|
| 1 | 21.6 |
| 2 | 20.5 |
| 3 | 15.0 |
| 4 | 10.6 |
| 5 | 20.1 |
| 6 | 21.4 |
| 7 | 69.8 |
| 8 | 12.4 |
| 9 | 16.4 |
| 10 | 19.4 |
| 11 | 69.7 |
| 12 | 17.0 |
| 13 | 39.7 |
| 14 | 34.3 |
| 15 | 17.5 |
| 16 | 18.0 |
| 17 | 22.8 |
| 18 | 24.6 |
| 19 | 63.2 |
| 20 | 32.9 |
| 21 | 20.7 |
| 22 | 20.1 |

In mouse plasma, mouse TGR23-2 ligand was detected in a higher level of 27.6±3.76 fmol/ml (mean±SEM, n=22).

EXAMPLE 7

Effects on Tumor Growth in Nude Mice by Administration of TGR23-2 Ligand-Neutralizing Antibody Effects on tumor growth in nude mice bearing the human colon cancer cell line LS 174T by administration of 23L-2Ca showing the neutralizing activity on TGR23-2 ligand were examined.

A solution of the colon cancer cell line LS 174T in PBS was injected subcutaneously into the left flank of female nude mice (BALB/cAnN-nu, 6 weeks old) in $2 \times 10^6$ cells/ 200 μl/mouse. On Day 10 after the administration, tumor size was measured and 24 out of 42 mice were chosen so as to make the size of tumor uniform and then the animal was divided into two groups each having 12 mice. The mice were injected intraperitoneally with 23L-2Ca and for control antibody, anti-human metastin monoclonal antibody (KIS-1Na) having the same IgG subclass structure (IgG1, κ) as in 23L-2Ca (Journal of Clinical Endocrinology & Metabolism, 88, 914-919, 2003) in a dose of 3 mg/kg/day for consecutive 14 days from the day of grouping. The size of tumor was measured every other day and the tumor volume was calculated in accordance with the formula: (long diameter)× (short diameter)$^2$/2.

Figure 10:
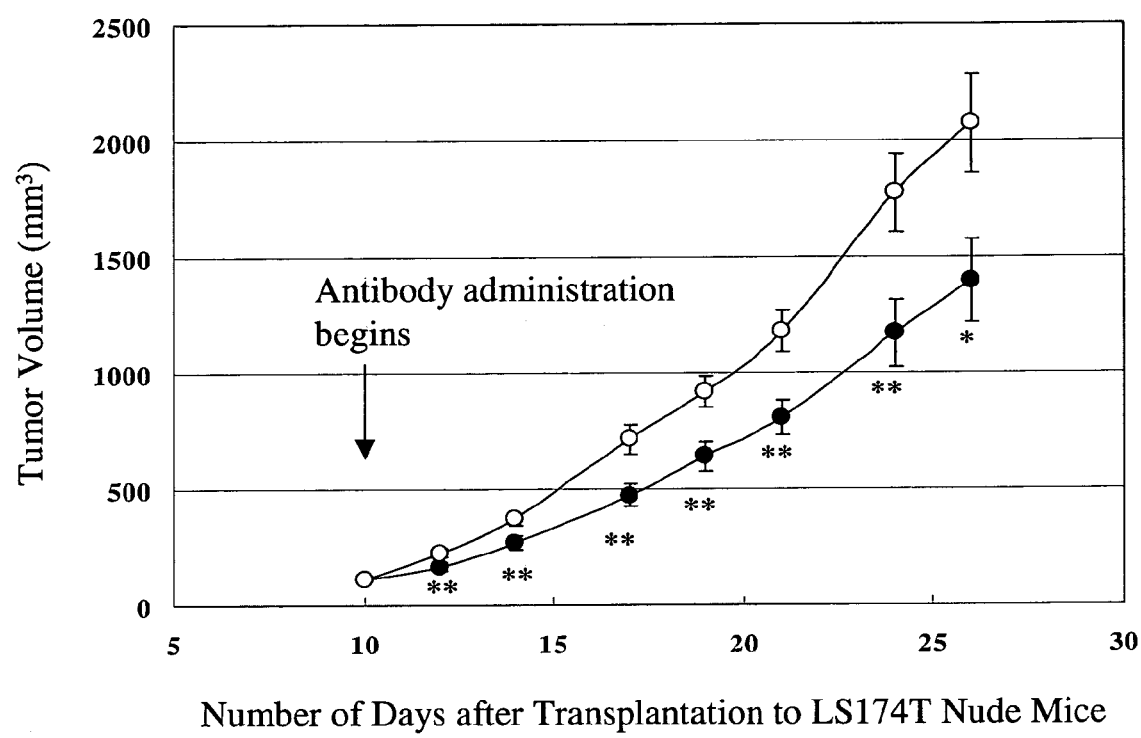
FIG. 10 shows tumor growth curves in human colon cancer cell line LS 174T-bearing nude mice after administration of 23L-2Ca showing the neutralizing activity on the TGR23-2 ligand and control antibody. In the figure, -●-(-closed circle-) represents the growth curve for the group administered with 23L-2Ca and -○-(-open circle-) represents the growth curve for the group administered with control antibody (KIS-1Na). Each value represents mean±standard error (mean±SE) (n=12). Symbol * indicates $p \leq 0.05$ when compared to the group administered with the control antibody (KIS-1Na). Symbol ** indicates $p \leq 0.01$ when compared to the group administered with the control antibody (KIS-1Na).

The results are shown in FIG. 10.

From the results, significant reduction in tumor volume LS 174T in the group administered with 23L-2Ca was observed during Days 2 to 17 from initiation of the administration.

EXAMPLE 8

Preparation of Amidated [Cys$^9$] Rat TGR23-2 Ligand (1-9) (SEQ ID NO: 5)

Commercially available p-methyl BHA resin (0.80 mmol/g resin) was charged in a reaction tank of peptide synthesizer ABI 430A. Then, Boc-amino acid derivatives of Boc-Cys (MeBzl), Boc-Ser(Bzl), Boc-Gly, Boc-Val, Boc-Asn and Boc-Arg(Tos) were introduced into the resin in this order, respectively, according to the Boc-strategy (NMP-HOBt) peptide synthesis to give the desired protected peptide resin. The resin, 0.21 g, was stirred at 0° C. for 60 minutes in 10 ml of anhydrous hydrogen fluoride containing 1.5 ml of p-cresol. Subsequently, the hydrogen fluoride was distilled off in vacuum. Diethyl ether was added to the residue and the precipitate was filtrated. The precipitate was extracted with 50% acetic acid aqueous solution and insoluble matters were removed. After the extract was sufficiently concentrated, the concentrate was applied to Sephadex (trade name) G-25 column (2.0×80 cm) filled with 50% acetic acid aqueous solution followed by development with the same solvent. The main fractions were collected and lyophilized to give 40 mg of white powders. A half volume of the powders was applied to chromatography column (2.6×60 cm) packed with LiChroprep (trade name) RP-18 followed by washing with 200 ml of 0.1% TFA-water. Linear gradient elution was then performed with 300 ml of 0.1% TFA-water and 300 ml of 0.1% TFA-containing 33% acetonitrile-water. The main fractions were collected and lyophilized to give 10 mg of the desired peptide.

Mass spectrum: M$^+$ 925.5 (calcd. 925.0)
Elution time on HPLC: 11.5 mins.
Elution conditions:
Column: Wakosil 5C18T (4.6×100 mm)
Eluent: linear density gradient elution (25 mins.) with Eluents A/B=95/5-45/55, using 0.1% TFA-water as Eluent A and acetonitrile containing 0.1% TFA as Eluent B.
Flow rate: 1.0 ml/min.

REFERENCE EXAMPLE 1

Preparation of Human TGR23-2 Ligand

Commercially available Boc-Ser(Bzl)-OCH$_2$-PAM resin was charged in a reaction tank of peptide synthesizer ACT90. After wetting with DCM, Boc was removed with TFA, followed by neutralization with DIEA. This resin was suspended in NMP and condensed with Boc-Lys(Cl-Z) using HOBt-DIPCI. After the reaction, a ninhydrin test was carried out to examine whether or not free amino group was present. When the ninhydrin test was positive, the same amino acid was recondensed. When the ninhydrin test was still positive even after recondensation, the amino group was acetylated with acetic anhydride. This cycle was repeated to condense Boc-Ala, Boc-Arg(Tos), Boc-Gln, Boc-Phe, Boc-Ser(Bzl), Boc-Thr(Bzl), Boc-Lys(Cl-Z), Boc-Lys(CL-Z), Boc-Met, Boc-Gly, Boc-Thr(Bzl), Boc-Gly, Boc-Val, Boc-Gly, Boc-Asn, Boc-Arg(Tos), Boc-Phe and Boc-Ser(Bzl) serially in this order to give 0.24 g of the desired protected peptide. After this resin was stirred at 0° C. for 60 minutes in about 15 ml of hydrogen fluoride containing 1.5 ml of p-cresol, the hydrogen fluoride was distilled off in vacuum. Diethyl ether was added to the residue and filtrated. Water and acetic acid were added to the filtrate and the peptide was extracted to separate from the resin. After the extract was concentrated, the concentrate was applied to Sephadex (trade name) G-25 column (2.0×80 cm) filled up with 50% acetic acid followed by development with the same solvent. The main fractions were collected and lyophilized. A part (45 mg) of the product was applied to reversed phase chromatography column (2.6×60 cm) packed with LiChroprep (trade name) RP-18 followed by washing with 200 ml of 0.1% TFA-water. Linear gradient elution was then performed with 300 ml of 0.1% TFA-water and 300 ml of 0.1% TFA-containing 33% acetonitrile-water. The main fractions were collected and lyophilized to give 12.7 mg of the desired peptide.

ESI-MS: molecular weight MW 2188.0 (calcd. 2187.5)
Elution time on HPLC: 10.6 mins.
Column conditions:
Column: Wakosil 5C18T 4.6×100 mm
Eluent: linear density gradient elution (25 mins.) with Eluents A/B=95 15-45/55, using 0.1% TFA-water as Eluent A and acetonitrile containing 0.1% TFA as Eluent B.
Flow rate: 1.0 ml/min.

REFERENCE EXAMPLE 2

Preparation of Rat TGR23-2 Ligand

Fmoc-Ala-OH was introduced into commercially available 2-chlorotrityl resin (Clt resin, 1.33 mmol/g) and 0.25 mmol of the resulting Fmoc-Ala-O-Clt resin (0.638 mmol/g) was charged in a reaction tank of peptide synthesizer ABI 433A. Solid phase synthesis was carried out using the Fmoc/DCC/HOBt strategy. As side chain protecting groups of Fmoc-amino acids, the Pbf group was used for Arg, the tBu group for Ser, the Boc group for Lys and the Trt group for Asn. Peptide chains from Arg at position 17 to Ser at position 14 in the sequence described above were sequentially introduced toward N-terminal direction, using those with unprotected side chains in the other amino acids. The Fmoc-rat TGR23-2 ligand (14-18)-O-Clt resin (0.25 mmol) obtained was treated with 381.1 mg (0.625 mmol) of Fmoc-Lys(Boc)-Thr(Psi(Me,Me)pro)-OH (manufactured by NOVA, product No. 05-20-1116), 326.1 mg (0.625 mmol) of PyAOP, 85.1 mg (0.625 mmol) of HOAt, 435.5 ml (2.5 mmol) of DIEA to introduce Lys at position 12 and Thr at position 13. Subsequently, solid phase synthesis on the peptide synthesizer was again carried out using the Fmoc-[Thr(Psi(Me,Me)pro)$^{13}$]-rat TGR23-2 ligand (12-18)-O-Clt resin obtained, whereby peptide chains from Lys at position 11 to Ser at position 1 were sequentially introduced toward the N-terminal direction to give 573.5 mg of the objective protected peptide resin.

After all of the resin (0.25 mmol) was stirred at room temperature for 90 minutes in 9 ml of a solution mixture of TFA, thioanisole, m-cresol, water, triisopropylsilane and ethanedithiol (80:5:5:5:2.5:2.5), ether was added to the reaction solution to precipitate white powders. After centrifugation, the supernatant was removed and this procedure was repeated 3 times. The residue was extracted with water and lyophilized to give 219.4 mg of white powders. The crude peptide thus obtained was applied on preparatory HPLC using YMC Pack R&D-ODS-5-B S-5, 120A column (30×250 mm) for linear density gradient elution (60 mins.) to A/B: 90/10-70/30 by Eluent A: 0.1% TFA-water, Eluent B: 0.1% TFA-containing acetonitrile. Fractions containing the product were collected and lyophilized to give white powders.

The powders obtained were all dissolved in water and 3 ml of the acetated resin obtained by converting ion exchange resin, AG1×8 100-200 mesh chloride form, manufactured by BIO-RAD, Corp. was added to the solution. After the mixture was stirred for 20 minutes and filtrated to remove the resin and impurities, the product was lyophilized and converted into the acetate to give 107.0 mg of white powders.

ESI-MS: $M^+$ 1954.2 (calcd. 1954.2)
Elution time on HPLC: 15.2 mins.
Elution conditions:
Column: YMC AM 301 (4.6×100 mm)
Eluent: linear density gradient elution (25 mins.) with Eluents A/B=100/0-50/50, using 0.1% TFA-water as Eluent A and acetonitrile containing 0.1% TFA as Eluent B.
Flow rate: 1.0 ml/min.

REFERENCE EXAMPLE 3

Preparation of Mouse TGR23-2 Ligand

Solid phase synthesis was carried out in the same manner as in the preparation of rat TGR23-2 ligand described in REFERENCE EXAMPLE 1, using 0.25 mmol (0.408 mmol/g) of the Fmoc-Gln(Trt)-O-Clt resin obtained by introducing Fmoc-Gln(Trt)-OH into commercially available 2-chlorotrityl resin (Clt resin, 1.12 mmol/g). Thus, 324.7 mg of the objective protected peptide resin was obtained.

This resin, 100 mg, was treated as in REFERENCE EXAMPLE 1 to give 50.0 mg of white powders. The crude peptide thus obtained was applied on preparatory HPLC using YMC SH-343-5 S-5, 120A column (20×250 mm) for linear density gradient elution (60 mins.) to A/B: 92/8-72/28 using Eluent A: 0.1% TFA-water, Eluent B: 0.1% TFA-containing acetonitrile. Fractions containing the product were collected and lyophilized to give 22.6 mg of white powders.

ESI-MS: $M^+$2182.8 (calcd. 2182.5)
Elution time on HPLC: 14.1 mins.
Elution conditions:
Column: YMC AM 301 (4.6×100 mm)
Eluent: linear density gradient elution (25 mins.) with Eluents A/B=100/0-50/50, using 0.1% TFA-water as Eluent A and acetonitrile containing 0.1% TFA as Eluent B.
Flow rate: 1.0 ml/min.

REFERENCE EXAMPLE 4

Preparation of [Cys[19]] Rat TGR23-2 Ligand (1-19) (SEQ ID NO: 4)

In a reactor of ABI 433A peptide synthesizer, 0.25 mmol (0.63 mmol/g) of H-Cys(Trt)-O-Clt resin commercially available was charged and solid phase synthesis was conducted using the Fmoc/DCC/HOBt strategy. To protect side chains of Fmoc-amino acids, the Pbf group was used for Arg, the tBu group for Ser, the Boc group for Lys and the Trt group for Asn. Peptide chains from Ala at position 18 to Ser at position 14 in the sequence described above were sequen-tially introduced toward N-terminal direction, using those with unprotected side chains in the other amino acids. After a half (0.125 mmol) out of the Fmoc-rTGR23L (14-18)-O-Clt resin (0.25 mmol) obtained was treated in 20% piperidine/DMF to remove the Fmoc group, Lys at position 12 and Thr at position 13 were introduced by treating with 304.9 mg (0.5 mmol) of Fmoc-Lys(Boc)-Thr($\Psi^{Me,Me}$Pro)-OH (manufactured by NOVA), 260.9 mg (0.5 mmol) of PyAOP, 1 ml (0.5 mmol) of 0.5M HOAt/DMF solution and 326.6 μl (1.88 mmol) of DIEA. Subsequently, solid phase synthesis on the peptide synthesizer was again carried out using the Fmoc-[Thr($\Psi^{Me,Me}$Pro)[13], Cys[19]] rat TGR23-2 ligand (12-19)-O-Clt resin obtained, whereby peptide chains from Lys at position 11 to Ser at position 1 were sequentially introduced toward the N-terminal direction to give 234.0 mg of the objective protected peptide resin.

After 100 mg of this resin was stirred in 1.5 ml of a solution mixture of TFA, thioanisole, m-cresol, $H_2O$, triisopropylsilane and ethanedithiol (80:5:5:5:2.5:2.5) at room temperature for 90 minutes, ether was added to precipitate white powders. Following centrifugation, the supernatant was removed and this procedure was repeated 3 times. The residue was extracted with aqueous acetic acid solution and lyophilized. The resulting white powders were applied on preparatory HPLC using YMC SH-343-5 S-5, 120A column (20×250 mm) for linear density gradient elution (60 mins.) to A/B: 86/14-76/24 by Eluent A: 0.1% TFA-water, Eluent B: 0.1% TFA-containing acetonitrile. Fractions containing the product were collected and lyophilized to give 26.1 mg of white powders.

Mass spectrum: $(M+H)^+$ 2056.6 (calcd. 2057.1)
Elution time on HPLC: 15.3 mins.
Elution conditions:
Column: YMC-AM301 (4.6×100 mm)
Eluent: linear density gradient elution (25 mins.) with Eluents A/B=100/0-50/50, using 0.1% TFA-water as Eluent A and acetonitrile containing 0.1% TFA as Eluent B.
Flow rate: 1.0 ml/min.

REFERENCE EXAMPLE 5

Effects of Human TGR23-2 Ligand on Feeding Level by Administration Into the Lateral Ventricle of Rats Rats were kept at room temperature of 25° C. under lighting from 8:00 to 20:00. Wistar male rats of 8 weeks old (body weights at operation: 260-280 g) were anesthetized by intraperitoneal administration of pentobarbital in a dose of 50 mg/kg and each animal was placed in a stereotaxic apparatus for the rat brain. The incisor bar was lowered by 3.3 mm from the interaural line. The skull was exposed, and using a dental drill a hole was made on the skull for implantation of a guide cannula AG-8 (inner diameter of 0.4 mm and an outer diameter of 0.5 mm, EICOM) was inserted into the lateral ventricle. In addition, anchor screws were buried in three positions around the drilled hole. A stainless-steel guide cannula AG-8 was inserted in such a manner that its leading end would be situated in the upper part of the lateral ventricle. With reference to the atlas of Paxinos and Watson (1998), the stereotaxic coordinates were AP: −0.8 mm, L: 1.5 mm and H: −4.5 mm from the bregma. The guide cannula was anchored to the skull by dental cement and anchor screws. A stainless-steel dummy cannula AD-8 (0.35 mm in outer diameter, EICOM) was then inserted through the guide cannula and locked in position with a cap nut (EICOM). After the operation, the rats were kept in individual cages and habituated to powder feed over a week.

After waiting for about a week after implantation of the guide cannula for postoperative recuperation and habituation to powder feed, the cap nut and dummy cannula were removed from the rat skull and instead, a stainless steel microinjection cannula AMI-9 (0.17 mm in inner diameter and 0.35 mm in outer diameter, EICOM) connected to a PTFE (polytetrafluoroethylene) tube (50 cm in length, 0.1 mm in inner diameter and 0.35 mm in outer diameter, EICOM) was inserted. The length of the microinjection cannula was adjusted beforehand to expose its tip by 1 mm from the guide cannula. One end of the PTFE tube was connected to a microsyringe pump and either OTSUKA distilled water or human TGR23-2 ligand dissolved in distilled water was injected, in a total volume of 10 µl (10 nmol/rat) into the lateral ventricle at a flow rate of 5 µl/min. On the lookout for 2 minutes after completion of the injection, the microinjection cannula was disconnected and the dummy cannula was anchored again with a cap nut. Injection was made from 19:00 to 20:00. The feeding level was then measured with passage of time at 30 minute intervals up to 4 hours after administration, using a feeding level measuring instrument Feed-Scale (Columbus, Inc.).

Figure 11:
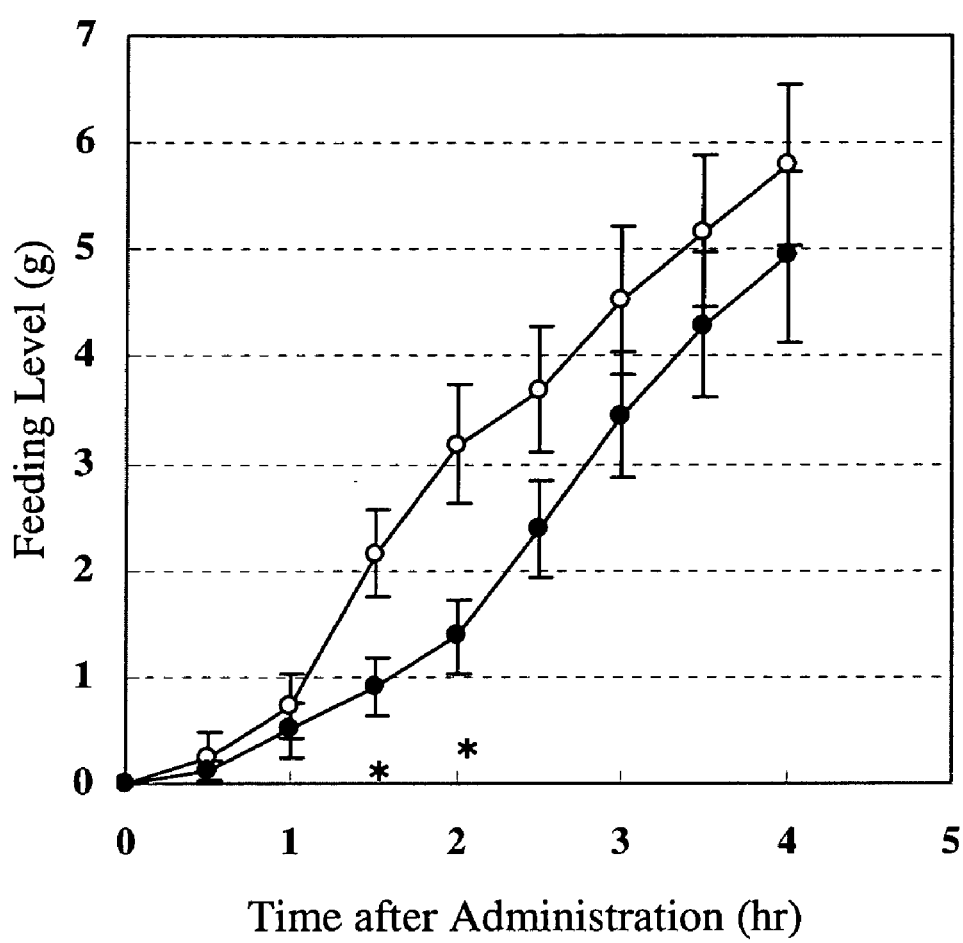
FIG. 11 shows changes in feeding levels with passage of time, when the feeding levels were measured every 30 minutes up to 4 hours after the administration of human TGR23-2 ligand or distilled water into the rat lateral ventricle. In the figure, -●-(-closed circle-) and -○-(-open circle-) represent the group administered with human TGR23-2 ligand and the group administered with distilled water, respectively. Each value represents mean±standard error (n=8). Symbol * indicates that the difference is significant ($p<0.05$) when compared to the group administered with distilled water.

The results are shown in FIG. 11.

From the results, significant ($p<0.05$) reduction in the feeding level was noted 1.5 and 2 hours after the administration in the human TGR23-2 ligand group, as compared to the control group.

INDUSTRIAL APPLICABILITY

The antibody of the present invention has an extremely high binding ability to the TGR23-2 ligand, can neutralize the intracellular $[Ca^{2+}]$ increasing activity of TGR23-2 ligand and has a tumor growth suppressing action. Accordingly, the antibody of the present invention can suppress the action of TGR23-2 ligand and hence can be used as a safe pharmaceutical, for example, as an agent for preventing/treating cancers (e.g., colorectal cancer, colon cancer, rectal cancer, breast cancer, lung cancer, non-small cell lung cancer, prostate cancer, esophageal cancer, gastric cancer, liver cancer, biliary tract cancer, spleen cancer, kidney cancer, bladder cancer, uterine cancer, ovarian cancer, cervical cancer, testicular cancer, thyroid cancer, pancreatic cancer, brain tumor, blood tumor, etc.) or anorexia, etc., or as an eating (appetite) stimulant, and so on; preferably as an agent for preventing/treating cancers. According to the assay methods using the antibody of the present invention, such as immunoassay by the sandwich technique using, e.g., the monoclonal antibody specifically recognizing the C-terminal region of TGR23-2 ligand (C-terminal region of the polypeptide comprising the amino acid sequence represented by SEQ ID NO: 2 or SEQ ID NO: 3, or a salt of the polypeptide) and the N-terminal region of TGR23-2 ligand, the TGR23-2 ligand can be specifically quantified with high sensitivity and can be used for diagnosis of, e.g., the diseases described above, etc. Furthermore, the antibody of the present invention can be used for immuno-tissue staining of the TGR23-2 ligand.

The invention claimed is:

1. An isolated monoclonal antibody that specifically binds to a peptide consisting of the $1^{st}$-$7^{th}$ amino acid residues of SEQ ID NO: 1.

2. The antibody according to claim 1, which has a neutralizing activity on the intracellular $Ca^{2+}$ion level increasing activity of a peptide comprising the amino acid sequence set forth as SEQ ID NO: 1.

3. The antibody according to claim 1, which is labeled.

4. The monoclonal antibody according to claim 1, which is designated as 23L-1Na and produced by a hybridoma designated 23L-1N (FERM BP-8302).

5. A hybridoma producing the monoclonal antibody according to claim 1.

6. The hybridoma according to claim 5, which is designated 23L-1N (FERM BP-8302).

7. A process of producing the monoclonal antibody according to claim 1, which comprises culturing a hybridoma producing the monoclonal antibody in vitro and collecting said monoclonal antibody.

8. A composition comprising the antibody according to claim 1.

* * * * *

UNITED STATES PATENT AND TRADEMARK OFFICE
CERTIFICATE OF CORRECTION

PATENT NO.        : 7,342,105 B2
APPLICATION NO.   : 10/547051
DATED             : March 11, 2008
INVENTOR(S)       : Hirokazu Matsumoto et al.

Page 1 of 1

It is certified that error appears in the above-identified patent and that said Letters Patent is hereby corrected as shown below:

On the Title Page, please delete Item "(73) Takeda Chemical Industries, Ltd., Osaka (JP)"

and insert Item -- (73) Takeda Pharmaceutical Company Limited, Osaka (JP) --

Signed and Sealed this

Seventeenth Day of June, 2008

JON W. DUDAS
*Director of the United States Patent and Trademark Office*

```
                            SEQUENCE LISTING

<160> NUMBER OF SEQ ID NOS: 5

<210> SEQ ID NO 1
    <211> LENGTH: 20
    <212> TYPE: PRT
    <213> ORGANISM: Homo sapiens

<400> SEQUENCE: 1

Ser Phe Arg Asn Gly Val Gly Thr Gly Met Lys Lys Thr Ser Phe Gln
                     5                   10                  15

Arg Ala Lys Ser
                20

<210> SEQ ID NO 2
    <211> LENGTH: 18
    <212> TYPE: PRT
    <213> ORGANISM: Rattus norvegicus

<400> SEQUENCE: 2

Ser Phe Arg Asn Gly Val Gly Ser Gly Val Lys Lys Thr Ser Phe Arg
                     5                   10                  15

Arg Ala

<210> SEQ ID NO 3
    <211> LENGTH: 20
    <212> TYPE: PRT
    <213> ORGANISM: Mus musculus

<400> SEQUENCE: 3
```

```
Ser Phe Arg Asn Gly Val Gly Ser Gly Ala Lys Lys Thr Ser Phe Arg
                 5                  10                  15

Arg Ala Lys Gln
            20

<210> SEQ ID NO 4
<211> LENGTH: 19
<212> TYPE: PRT
<213> ORGANISM: Artificial Sequence
<220> FEATURE:
<223> OTHER INFORMATION: immunogen

<400> SEQUENCE: 4

Ser Phe Arg Asn Gly Val Gly Ser Gly Val Lys Lys Thr Ser Phe Arg
                 5                  10                  15

Arg Ala Cys

<210> SEQ ID NO 5
<211> LENGTH: 9
<212> TYPE: PRT
<213> ORGANISM: Artificial Sequence
<220> FEATURE:
<223> OTHER INFORMATION: the C-terminus of the polypeptide is amide
      (-CONH2) form

<400> SEQUENCE: 5

Ser Phe Arg Asn Gly Val Gly Ser Cys
                 5
```